(12) United States Patent
Soejima et al.

(10) Patent No.: US 10,054,568 B2
(45) Date of Patent: Aug. 21, 2018

(54) SYSTEM AND METHOD FOR DAMAGE DIAGNOSIS

(71) Applicants: Hideki Soejima, Tokyo (JP); Yoji Okabe, Tokyo (JP)

(72) Inventors: Hideki Soejima, Tokyo (JP); Yoji Okabe, Tokyo (JP)

(73) Assignees: SUBARU CORPORATION, Tokyo (JP); THE UNIVERSITY OF TOKYO, Tokyo (JP)

( * ) Notice: Subject to any disclaimer, the term of this patent is extended or adjusted under 35 U.S.C. 154(b) by 903 days.

(21) Appl. No.: 14/335,182

(22) Filed: Jul. 18, 2014

(65) Prior Publication Data

US 2014/0330528 A1   Nov. 6, 2014

Related U.S. Application Data

(62) Division of application No. 13/047,517, filed on Mar. 14, 2011.

(30) Foreign Application Priority Data

Mar. 16, 2010   (JP) .................................. 2010-058784

(51) Int. Cl.
*G01N 29/04*   (2006.01)
*G01N 29/44*   (2006.01)
(Continued)

(52) U.S. Cl.
CPC ......... *G01N 29/4436* (2013.01); *G01N 29/07* (2013.01); *G01N 29/46* (2013.01);
(Continued)

(58) Field of Classification Search
CPC .... G01N 29/07; G01N 29/46; G01N 29/4436; G01N 2291/011; G01N 2291/0427; G01N 2291/0289
(Continued)

(56) References Cited

U.S. PATENT DOCUMENTS 5,814,730 A *   9/1998   Brodeur ................. G01N 29/07
                                                              73/159
2008/0255778 A1*  10/2008  Liu ....................... G01N 29/041
                                                              702/35
(Continued)

FOREIGN PATENT DOCUMENTS

JP   2005-098921   4/2005
JP   2007-023271   2/2007

*Primary Examiner* — Yoshihisa Ishizuka
(74) *Attorney, Agent, or Firm* — Konomi Takeshita

(57) ABSTRACT

The object of the invention is to provide a damage diagnostic system that uses a damage detection system that obtains propagation intensity distribution data, which is expanded in the two dimensions frequency and propagation time, by converting the output value from an oscillation detection sensor that was obtained when oscillation is performed by an oscillator, and for one mode or two or more modes that are selected from the fundamental mode and higher mode of Lamb waves, obtains certain characteristic values from the data, for example three indices, which are the slope of the mode dispersion of the A1 mode (rate of change of the propagation time with respect to the frequency), the amount of decrease in the propagation time of the A1 mode, and the amount of increase in the propagation time of the S0 and S1 modes, and outputs the measurement results. The measurement results are displayed on a display device.

10 Claims, 26 Drawing Sheets

(51) Int. Cl.
  *G01N 29/07* (2006.01)
  *G01N 29/46* (2006.01)
(52) U.S. Cl.
  CPC .............. *G01N 2291/011* (2013.01); *G01N 2291/0289* (2013.01); *G01N 2291/0427* (2013.01)
(58) Field of Classification Search
  USPC .......................................................... 702/39
  See application file for complete search history.

(56) References Cited

U.S. PATENT DOCUMENTS

2009/0301198 A1* 12/2009 Sohn .................... G01N 29/069
  73/598
2011/0041612 A1* 2/2011 Paige ................. G01N 29/2412
  73/623

* cited by examiner

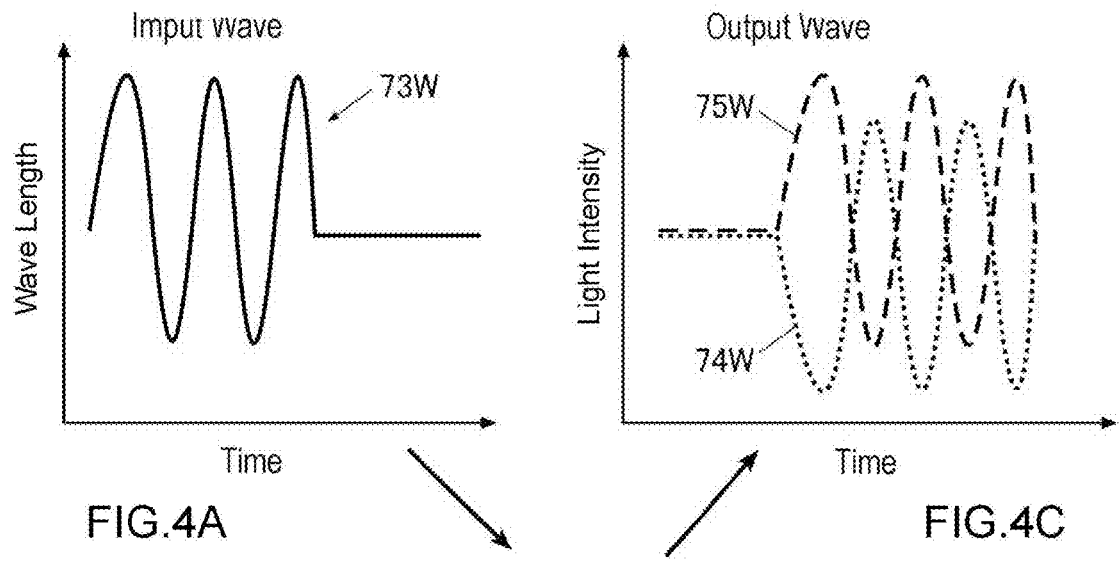
FIG.4A
FIG.4C
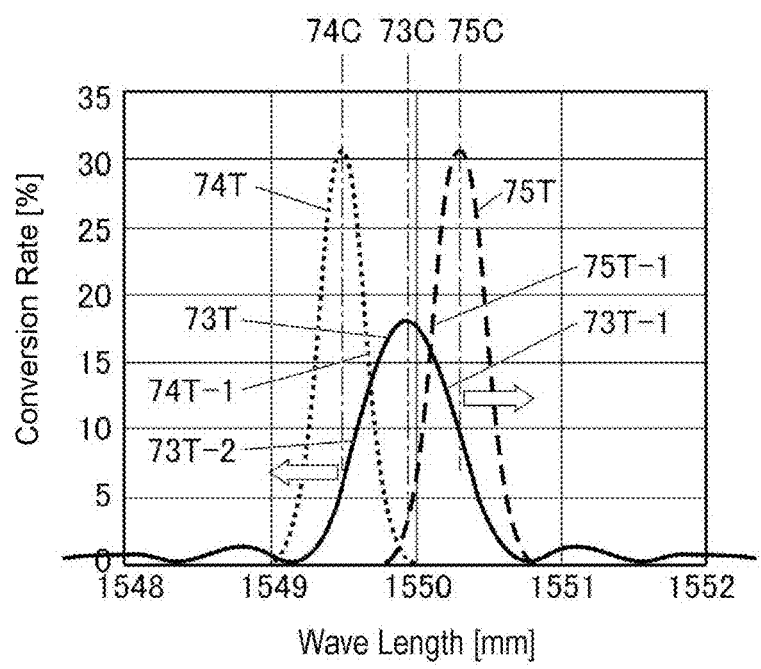
FIG.4B

Status is Healthy

With a Peeling between Layers

Each number in < > is dimension [mm]

SYSTEM AND METHOD FOR DAMAGE DIAGNOSIS

CROSS REFERENCE TO RELATED APPLICATIONS

This is a divisional of co-pending U.S. patent application Ser. No. 13/047,517, filed on Mar. 14, 2011, which claims priority from Japanese Patent Application Serial No. 2010-058784, filed on Mar. 16, 2010. The entire disclosure of the aforesaid application is incorporated herein by reference.

FIELD OF THE INVENTION

The present invention relates to a system and method for damage diagnosis that uses Lamb waves.

BACKGROUND OF THE INVENTION

In fields where strength and weight reduction of materials are required, for example in the field of fuselage of an aircraft, in order to meet such demands, the use of many composite materials such as CFRP (Carbon Fiber Reinforced Plastics) is essential. In order to maintain a high level of reliability of structures made from such composite materials and to perform more efficient design work, damage detection technology (health monitoring technology) is attracting much attention. As devices for performing this kind of detection of damage and defects in composite materials, there are damage detection devices as disclosed in patent publication 1 and 2 that use a FBG (Fiber Bragg Grating) optical fiber sensor. Recently, optical fibers are becoming very thin (for example, 52 µm diameter). As a result, even when embedded in a structure, there is not much of a decrease in strength of the structure. Therefore, optical fibers have an advantage that they have a high degree of freedom regarding placement.

The inventions disclosed in Japanese patent publication 1 and 2 below use an optical fiber sensor having a grating section wherein piezo elements that are fixed and arranged at specified locations in a structural composite material, lead wires that transmit signals to the piezo elements, an optical fiber sensor attached to the structural composite material so that the composite material of the structural composite material is located between the optical fiber sensor and the piezo elements, the optical fiber sensor having a grating section to reflect light of a specified wavelength to a core section, a light source that shines light on the core section, and a characteristic detection unit that detects a characteristic of the reflected light from the grating section, and vibrating the material by the piezo elements, detects damage from the change in output from the characteristics detection unit. A spectrum analyzer that detects the frequency characteristic of reflected light from the grating section is used as the characteristic detection unit.

Furthermore, in the invention disclosed in Japanese Patent Publication No. 2005-098921, a comparison is performed with detected data of a normal structural composite material that was acquired beforehand. Alternatively, another method is disclosed in which in the frequency distribution that is detected by the spectrum analyzer, a threshold value is set for the fluctuation value from when there is no oscillation of a specified frequency, and when the detected value is equal to or less than that threshold value, it may be determined that there is damage (paragraph 0032).

In the invention disclosed in Japanese Patent Publication No. 2007-232371, two optical filters are provided in a spectrum analyzer. It is proposed that by outputting reflected light to an arithmetic processing unit via the two optical filters, the spectrum analyzer will detect a wavelength oscillation signal of the reflected light with high sensitivity. It is also proposed that the arithmetic processing unit will calculate a value (DI value) that corresponds to the scale of the damage of the test object based on the obtained wavelength oscillation signal.

As a method of damage detection technology, research is being performed regarding a method in which ultrasonic waves called Lamb waves are generated and detected, and the occurrence of damages is diagnosed based on the change in the detected waves. The Lamb wave is an ultrasonic wave that propagates through a thin plate, and propagates over a long distance with a relatively small amount of damping. Therefore, it is a form of ultrasonic wave propagation that is suitable to damage detection. Moreover, Lamb waves have two characteristics; a multi-mode characteristic and velocity dispersion characteristic (frequency dependence), and depending on the plate thickness and frequency, there are plurality of modes having different speeds. Due to these complex characteristics, conventionally, damage detection was performed by using only information about a specific frequency of the Lamb waves.

SUMMARY OF THE INVENTION

Considering the above situation, the purpose of the present invention is to provide a system and method for damage diagnosis that use the dispersion characteristic of Lamb waves in order to make it possible to measure the mode dispersion over a broad band frequencies, make it possible to perform quantitative evaluation of the peeling length by obtaining more useful information for damage detection than in conventional technology, and make it possible to detect and diagnose damages with high precision and high reliability According to a first embodiment of the present invention to achieve the purpose described above, there is provided a system for damage diagnosis for diagnosing a damage that occurred on or within an object, the system comprising:

an oscillator for applying a broadband ultrasonic oscillation to the object to generate a broadband Lamb wave within the object;

an oscillation detection sensor for detecting the broadband Lamb wave from the object, the detected broadband Lamb wave having at least one mode of Lamb wave; and a processing unit, being connected to the oscillator and the oscillation detection sensor, for (1) obtaining a time-frequency transformation data by performing a time-frequency transformation to the broadband Lamb wave detected by the oscillation detection sensor, wherein the time-frequency transformation data indicates a propagation time of the at least one mode of Lamb wave, and the propagation time is the time for Lamb wave to propagate from the oscillator through the oscillation detection sensor, and (2) identifying, based on the propagation time of the at least one mode of Lamb wave in the time-frequency transformation data, whether or not the damage has occurred on or within the object, and/or identifying the size or length of the damage that occurred on or within the object.

According to a second embodiment of the present invention to achieve the purpose described above, there is provided the system for damage diagnosis according to the first embodiment, wherein the time-frequency transformation data obtained by the processing unit is a two-dimensional propagation intensity distribution data in which frequency is one of the two dimension and propagation time is the other.

According to a third embodiment of the present invention to achieve the purpose described above, there is provided the system for damage diagnosis according to the first embodiment, wherein the at least one mode Lamb wave includes a plurality of waves having mutually different frequencies; and the propagation time of the at least one mode of Lamb wave is a propagation time of the maximum intensity portion of at least one of the plurality of waves.

According to a fourth embodiment of the present invention to achieve the purpose described above, there is provided the system for damage diagnosis according to the first embodiment, wherein the identifying process (2) comprises a selection step for selecting the at least one mode Lamb wave among the two or more modes of Lamb waves to be compared with the reference value.

According to a fifth embodiment of the present invention to achieve the purpose described above, there is provided the damage diagnostic system according to the first embodiment, wherein the at least one mode is the S0 mode and S1 mode.

According to a sixth embodiment of the present invention to achieve the purpose described above, there is provided the damage diagnostic system according to the first embodiment, wherein the at least one mode is the A1 mode, S0 mode, and S0 mode.

According to a seventh embodiment of the present invention to achieve the purpose described above, there is provided the system for damage diagnosis according to the first embodiment, wherein the at least one mode Lamb wave includes a plurality of waves having mutually different frequencies; and the processing unit, in the identifying process (2), calculates propagation times of two of the plurality of waves, calculates a change ratio of the propagation times by means of dividing a difference of the two propagation times by a difference of the frequencies of the two waves, and based on whether or not the change ratio matches the reference value, identifies whether or not damage has occurred on or within the object, and/or identifies the size or length of the damage that occurred on or within the object.

According to an eighth embodiment of the present invention to achieve the purpose described above, there is provided the damage diagnostic system according to the seventh embodiment, wherein the at least one mode is the A1 mode.

According to a ninth embodiment of the present invention to achieve the purpose described above, there is provided the system for damage diagnosis according to the fourth embodiment, wherein the system comprises two oscillators, with one oscillator being attached to one surface in the thickness direction of the object, and the other oscillator being attached to the other surface in the thickness direction of the object; and the processing unit executes an oscillation control process to control the oscillators, and executes the oscillation control process and the selection step under any of the conditions (a) to (c) below, where condition (a) is such that the processing unit, in the oscillation control process, controls the two oscillators so that a symmetrical mode Lamb wave is generated in the object, and selects the symmetric mode Lamb wave in the selection process;

condition (b) is such that the processing unit, in the oscillation control process, controls the two oscillators so that a asymmetric mode Lamb wave is generated in the object, and selects the asymmetric mode Lamb wave in the selection process; and condition (c) is such that the processing unit executes the processes under conditions (a) and the processes under condition (b) at different times.

According to a tenth embodiment of the present invention to achieve the purpose described above, there is provided the system for damage diagnosis according to the fourth embodiment, wherein this system comprises two oscillation detection sensors, with one oscillation detection sensor being attached to one surface in the thickness direction of the object, and the other oscillation detection sensor being attached to the other surface in the thickness direction of the object; and the processing unit executes the processes (1) and (2) under any one of the conditions (a) to (c) below; where condition (a) is such that the processing unit, in the obtaining process (1), creates data in which the asymmetric mode is canceled out and the symmetric mode is emphasized by adding the broadband Lamb waves detected by the two oscillation detection sensors, and then the processing unit obtains time-frequency transformation data by performing the time-frequency transformation to the created data, and in the identifying process (2), selects a symmetric mode Lamb wave;

condition (b) is such that the processing unit, in the obtaining process (1), creates data in which the symmetric mode is canceled out and the asymmetric mode is emphasized by subtracting the broadband Lamb waves detected by the two oscillation detection sensors, and then the processing unit obtains time-frequency transformation data by performing the time-frequency transformation to the created data, and in the identifying process (2), selects a asymmetric mode Lamb wave; and condition (c) is such that the processing unit executes the processes under conditions (a) and the processes under condition (b).

According to an eleventh embodiment of the present invention to achieve the purpose described above, there is provided a method for damage diagnosis for diagnosing a damage that occurred on or within an object, the method using an oscillator for applying a broadband ultrasonic oscillation to the object to generate a broadband Lamb wave within the object, an oscillation detection sensor for detecting the broadband Lamb wave from the object, the detected broadband Lamb wave having at least one mode of Lamb wave, and a processing unit being connected to the oscillator and the oscillation detection sensor, and the method comprises the steps of:

(1) obtaining a time-frequency transformation data by performing a time-frequency transformation to the broadband Lamb wave detected by the oscillation detection sensor, wherein the time-frequency transformation data indicates a propagation time of the at least one mode of Lamp wave, and the propagation time is the time for Lamb wave to propagate from the oscillator through the oscillation detection sensor; and (2) identifying, based on the propagation time of the at least one mode of Lamb wave in the time-frequency transformation data, whether or not the damage has occurred on or within the object, and/or identifying the size or length of damage that occurred on or within the object.

As Lamb waves, there is a Lamb wave of Symmetric mode (S mode) which has symmetric amplitude relative to the center in the thickness direction of the oscillation propagation object having a plate-like shape, and a Lamb wave of Asymmetric mode (A mode) which has asymmetric amplitude relative to the center of the thickness direction of the oscillation propagation object. Also, there are plural n dimension modes (Sn, An) which are respectively higher dimension modes of the fundamental symmetric mode (S0) and the fundamental asymmetric mode (A0). Therefore, the waveform of the Lamb wave becomes complicated.

In the research conducted by the inventors, a method to divide the symmetric and asymmetric modes by means of generating and detecting a broadband Lamb wave was established. As a result of analyzing each mode using this method, it is found that S1 mode is transformed to S0 and A1 modes at a peeling portion occurred between layers, those modes propagate through the peeling portion, those modes go back to S1 mode again after having passed the peeling portion, and that S1 mode propagates through the object.

Also, it is found that A1 mode is transformed at the peeling portion to S0 mode which has a propagation speed faster than that of A1 mode, the S0 mode propagates through the peeling portion, the S0 mode goes back to A1 mode again after having passed the peeling portion, and the A1 mode propagates through the object Thus, the change of velocity leads to the change of arrival time. Also, it is found that the arrival time of each mode shows its particular change in accordance with the length of the peeling portion.

Therefore, by obtaining a two-dimensional propagation intensity distribution data that is expanded 2-dimensionally according to frequency and propagation time, and by obtaining from the data, as to a specified mode, a predetermined characteristic value (index which represents size of the damage) which shows the change of the arrival time of the objective mode that occurs by the damage, it becomes possible to determine as to whether or not the damage has occurred, and as to the size of the damage.

Other features and advantages of the present invention will become apparent from the following detailed description, taken in conjunction with the accompanying drawings, which illustrate, by way of example, the principles of the invention.

BRIEF DESCRIPTION OF THE DRAWINGS

FIG. 4A is a diagram of an input waveform that is inputted to an optical filter of an embodiment of the present invention, FIG. 4B is a spectrum of the passbands of two optical filters, and FIG. 4C is an output waveform of the optical filter.

FIG. 19A is for when the overall structure is healthy, and FIG. 19B is for when peeling occurs.

DETAILED DESCRIPTION OF THE INVENTION

In the following, a preferred embodiment of the present invention will be described in detail with reference to the accompanying, exemplary diagrams. The following is only an embodiment and does not limit the present invention.

[Basic Configuration]

First, the basic configuration of the damage detection system of this embodiment is explained below.

Figure 1:
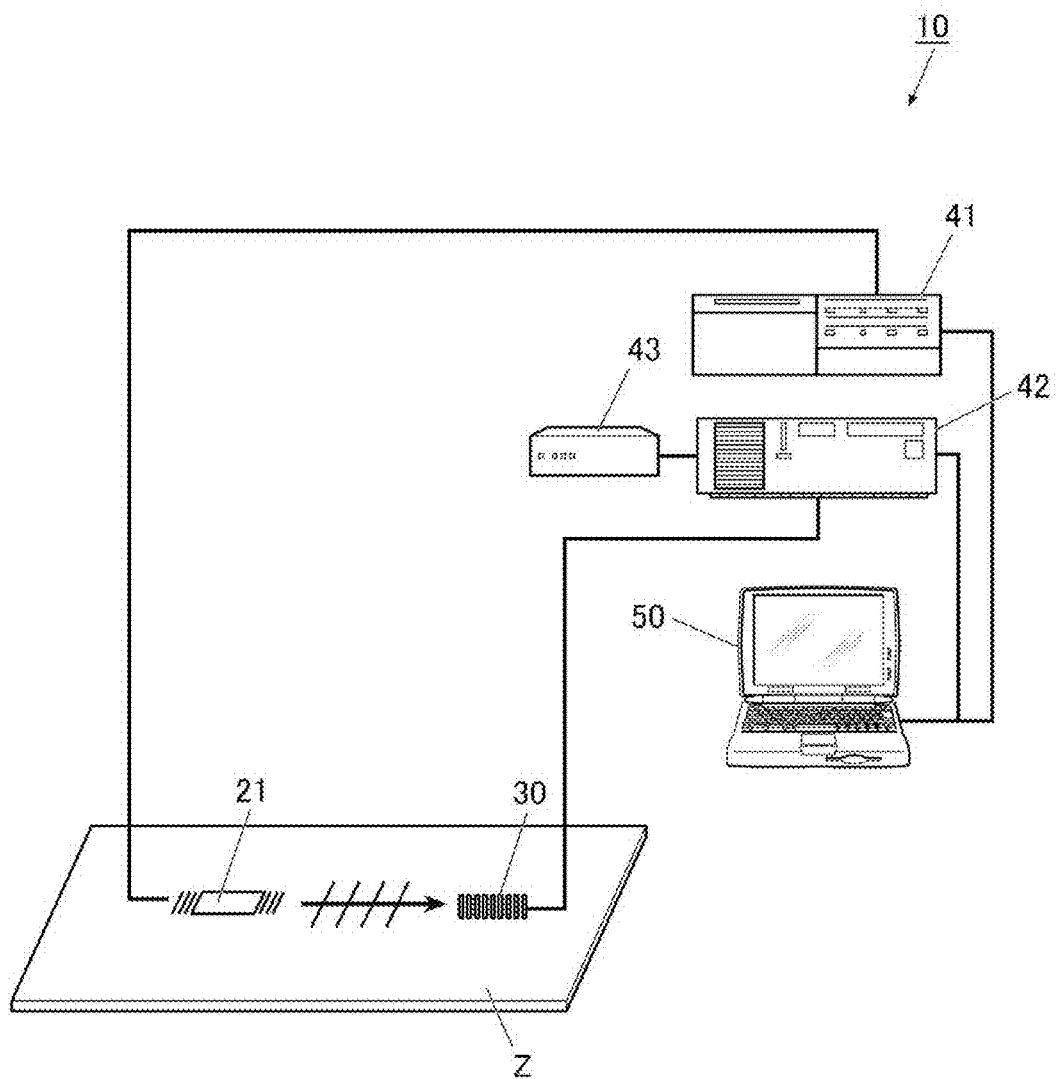
FIG. 1 is a diagram illustrating the configuration of a damage detection system of an embodiment of the present invention.

FIG. 1 is a diagram illustrating the configuration of a damage detection system 10 that detects damage in a structural composite material Z. In this embodiment, the structural composite material is the test object for which detection is performed.

In this embodiment, an MFC (Macro Fiber Composite) actuator is used as an oscillator for applying Lamb wave type ultrasonic wave oscillation to a test object. The MFC actuator has ultra thin rectangular column shaped piezoelectric ceramic lined up in one direction and embedded in an epoxy resin, with electrodes being adhered to the upper and lower surfaces, and is capable of causing a relatively large in-plane strain to occur in one direction. Because of that characteristic, it is known that an MFC actuator can also be used as an ultrasonic oscillation element. It is also possible to apply another kind of oscillation actuator, such as piezoelectric elements as the oscillator.

As illustrated in FIG. 1, the damage detection system 10 of this embodiment comprises: an MFC actuator 21 that is adhered to the surface section of a structural composite material Z near the location where damage detection of the structural composite material Z is to be performed; an optical fiber sensor 30 as an oscillation detection sensor that is placed near the location where damage detection of the structural composite material Z is to be performed; a controller 41 for controlling the MFC actuator 21; a spectrum analyzer 42 that detects the wavelength characteristic of reflected light that is obtained from the optical fiber sensor 30; and an arithmetic processing unit 50 that performs arithmetic processing of output values from the spectrum analyzer 42. The power source 43 for the spectrum analyzer 42 is also illustrated in the figure.

When a driving voltage is applied from the outside, the MFC actuator 21 causes a relatively large in-plane strain to occur in one direction in that plane. Using this, the controller 41 applies a driving voltage to the MFC actuator 21 in order to apply an instantaneous oscillation to the structural composite material Z.

Figure 2A:
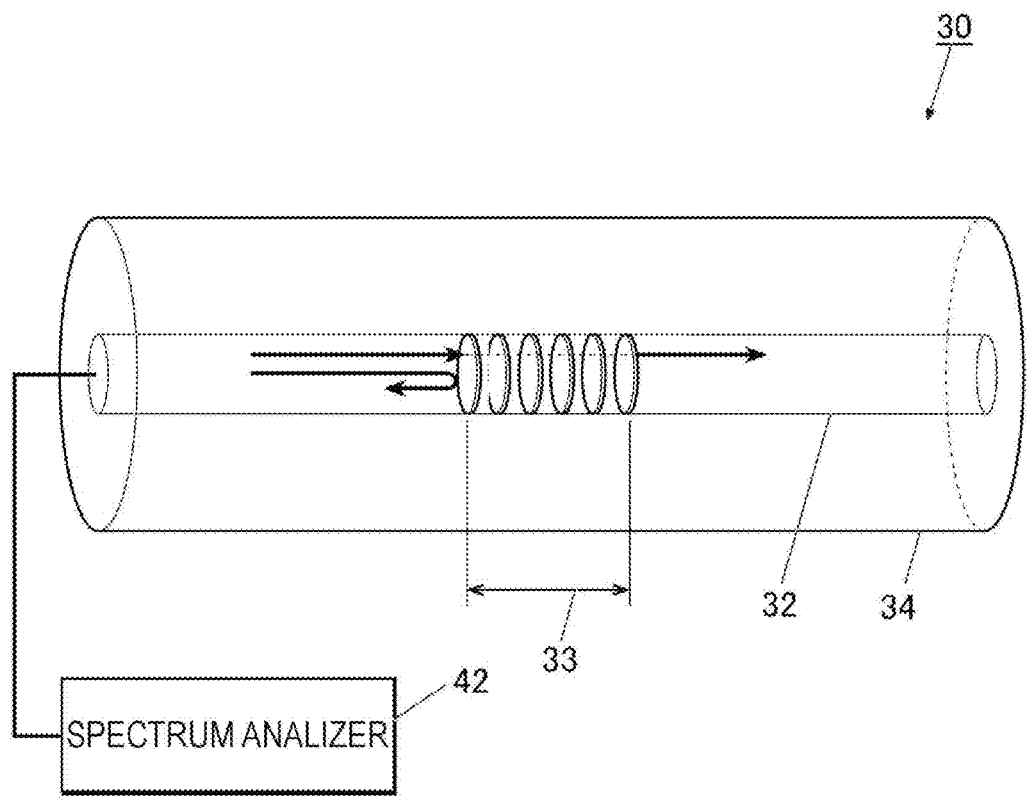
FIG. 2A is a diagram illustrating the construction of an optical fiber sensor.

The optical fiber sensor 30 is an FBG (Fiber Bragg Grating) optical fiber sensor, and as illustrated in FIG. 2A is made from an optical fiber 34 having a grating section 33 located inside the core section 32 that reflects light of a certain wavelength.

One of the end sections of the optical fiber 34 is connected to the spectrum analyzer 42, and light covering a specified range of wavelength bands is irradiated from the light source of that spectrum analyzer 42 and enters into the core section 32. The light that enters from the spectrum analyzer 42 propagates through the core section 32 and only some of the light wavelengths are reflected by the grating section 33.

Figure 2B:
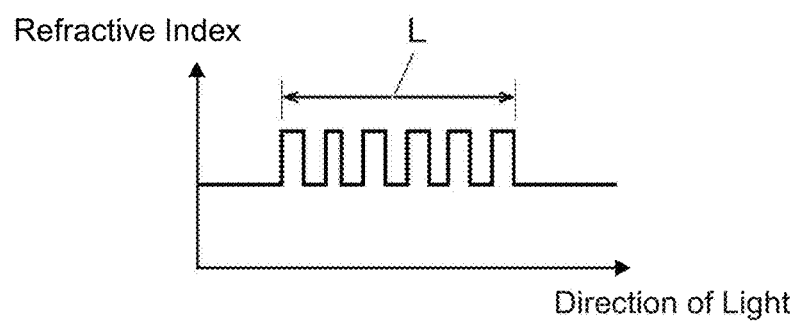
FIG. 2B is a line diagram illustrating the change in the index of refraction of the grating section in the direction that light advances.

FIG. 2B is a line diagram illustrating change in the refractive index in the advancement direction of the light through the core section 32, and in the figure, the range L illustrates the refractive index in the grating section 33.

As illustrated in the figure, the grating section 33 is constructed such that the refractive index of the core section 32 changes at a fixed cycle. The grating section 33 selectively reflects only light of certain wavelength at the boundary sections where the refractive index changes.

Here, the change in the wavelength $\Delta\lambda B$ of the reflected light from the FBG optical fiber sensor is represented by equation (1) below where n is the effective refractive index of the core, $\Lambda$ is the grating interval, P11 and P12 are Pockels coefficients, $\nu$ is the Poisson's ratio, $\varepsilon$ is the applied strain, $\alpha$ is the temperature coefficient of the fiber material and $\Delta T$ is the change in temperature (Alan D. Kersey, "Fiber Grating Sensors", JOURNAL OF LIGHTWAVE TECHNOLOGY, Vol. 15, No. 8, 1997).

[Formula 1]

$$\Delta\lambda_B = 2n\Lambda\left(\left\{1-\left(\frac{n^2}{2}\right)[P_{12}-\nu(P_{11}+P_{12})]\right\}\varepsilon + \left[\alpha + \frac{\left(\frac{dn}{dT}\right)}{n}\right]\Delta T\right) \quad (1)$$

Therefore, when oscillation occurs in the grating section 33, the amount of strain $\varepsilon$ in the grating section 33 changes, and as a result, the wavelength of the reflected light fluctuates according to the amount of strain $\varepsilon$. As long at the oscillation is transmitted in a good manner from the oscillation source, the grating section 33 generates a large strain, and the amount of change in the wavelength $\Delta\lambda B$ fluctuates a lot, however when the oscillation is not transmitted in a good manner from the oscillation source, the grating section 33 generates small strain, and the amount of change in the wavelength $\Delta\lambda B$ fluctuates only a little.

The MFC causes strain orthogonal to the axial direction of the fibrous piezoelectric element to occur, and the FBG detects strain in the axial direction that occurred in the fibrous optical fiber. These elements have a wide frequency characteristic without having a resonant frequency, and because these elements have strong directivity, the propagation path is distinct. Using these two characteristics, the measurement system of this embodiment is able to allow propagation of broadband Lamb waves having directivity. The FBG and MFC are both compact and lightweight, are flexible and have a high failure strain, so can be integrated with a laminated plate, they will not fail even under large strain, so have high reliability, and having such characteristics are suitable for use in structural health monitoring.

Figure 3A:
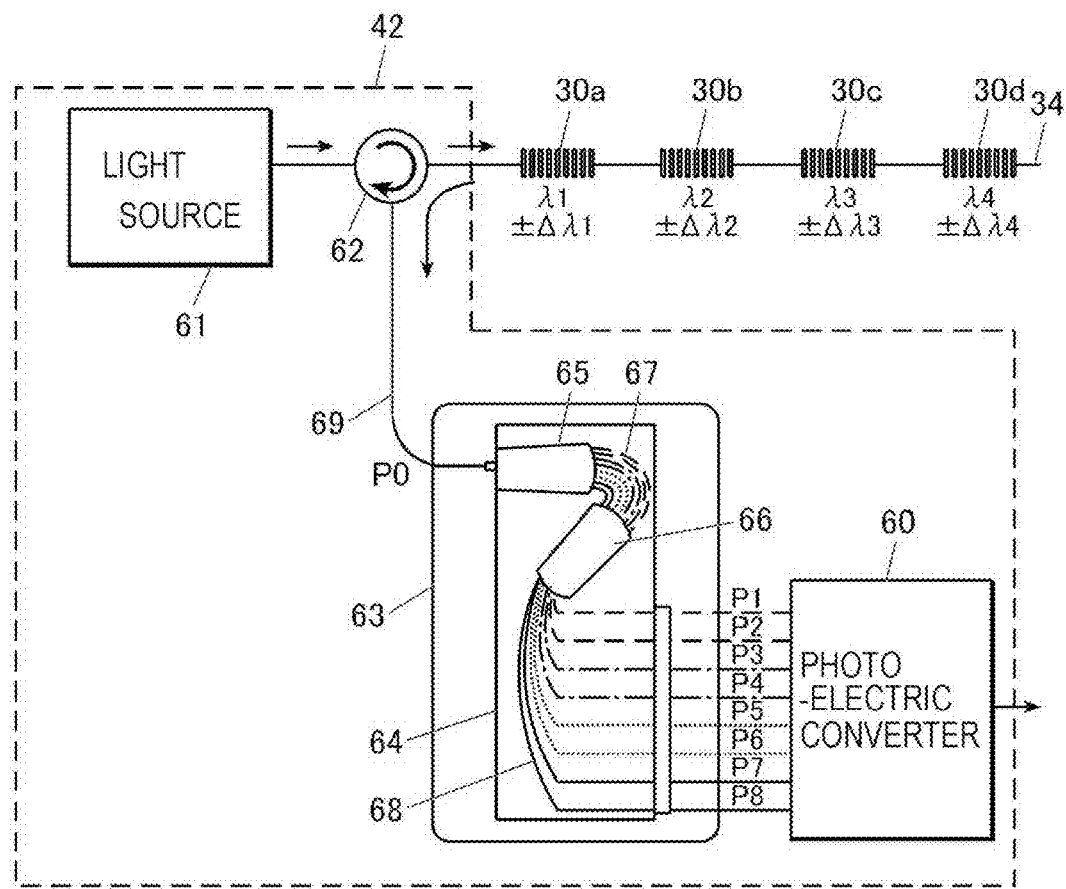
FIG. 3A is a diagram illustrating the construction of an optical fiber sensor and the spectrum analyzer that is connected to the optical fiber sensor of an embodiment of the present invention.

FIG. 3A illustrates an example of the construction of the optical fiber sensors and the spectrum analyzer that is connected to the sensors. As illustrated in FIG. 3A, the spectrum analyzer 42 comprises a light source 61, an optical circulator 62, an AWG module 63 and a photoelectric converter 60. In this embodiment, an optical fiber 34, in which four optical fiber sensors 30a to 30d having different reflected wavelengths are arranged in series, is connected to the spectrum analyzer 42. The minimum structure is the optical sensors 30.

The light source 61 is a broadband light source that includes all of the oscillation areas of the reflected wavelengths of the optical fiber sensors 30a to 30d. This is so that even when there is oscillation at the reflected wavelengths of the optical sensors 30a to 30d due to a Lamb wave, it is always possible to obtain the fully reflected light.

The optical circulator 62 causes light from the light source 62 to advance toward the optical fiber sensors 30a to 30d, and directs the reflected light from the optical fiber sensors 30a to 30d to the optical fiber 69. The reflected light that is guided to the optical fiber 69 is led to the input port P0 of the AWG module 63.

The AWG module 63 has an AWG substrate 64. A monolithic integrated lightwave circuit is formed on the AWG substrate 64. The lightwave circuit on the AWG substrate 64 has input/output slab waveguides 65, 66, an array waveguide 67 and an output waveguide 68, and forms eight optical filters having different passbands that are connected in parallel to the input port P0. The lightwave circuit on the AWG substrate 64 divides the wavelength multiplexed input light into different wavelengths by passing the light through the eight optical filters, and outputs that light in parallel to eight output ports P1 to P8. However, the actual number of output ports is not limited to eight.

Figure 3B:
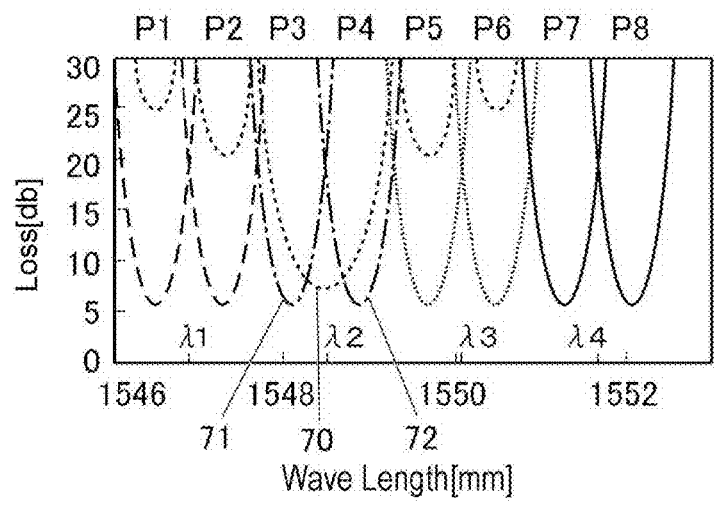
FIG. 3B is diagram illustrating a spectrum of the passband of eight optical filters.

Each of the passbands of the optical filters that corresponds to the eight output ports P1 to P8 are illustrated in the spectrum in FIG. 3B. For example, in FIG. 3B, the reflected light that corresponds to the portion where the reflected light input distribution 70 of the optical fiber sensor 3b that has a center reflected wavelength of λ2 overlaps passband 71 is allowed to pass through one of the optical filters and is outputted to the output port P3, and at the same time, the reflected light that corresponds to the portion that overlaps passband 72 is allowed to pass through another optical filter and is outputted to the output port P4. Similarly, output ports P1 and P2 correspond to the optical fiber sensor 30a having a center reflected wavelength of λ1, output ports P5 and P6 correspond to the optical fiber sensor 30c having a center reflected wavelength of λ3, and output ports P7 and P8 correspond to the optical fiber sensor 30d having a center reflected wavelength of λ4, and dividing the wavelengths is possible in the same way. As described above the minimum structure is one optical fiber sensor, and in this case two optical filters are sufficient.

On behalf of all, the processing that is performed on the reflected light from one optical fiber sensor 30 will be explained with reference to FIGS. 4A and 4B.

As illustrated in FIG. 4B, an input distribution 73T of the reflected light from the optical fiber sensor 30 appears. When oscillation is applied by the MFC actuator 21, a Lamb wave, having the MFC actuator as the oscillation source, propagates through the structural composite material Z, and the optical fiber sensor 30 causes oscillation at the wavelength of the outputted reflected light according to the Lamb wave that is transmitted from the structural composite material Z. The oscillation at this wavelength is graphically illustrated by input wave 73W in FIG. 4A.

Due to the oscillation at this wavelength, the reflected light input distribution 73T illustrated in FIG. 4B alternately shifts upward and downward a little, so there is a repeated increase and decrease in the wavelength value.

At such a wavelength oscillation, 73C in the figure is the oscillation center having the center wavelength of the reflected light input distribution 73T. On the other hand, the center wavelength 75C of the passband 75T of the optical filter is fixed in the area above the oscillation center 73C.

Moreover, the center wavelength 75C and center wavelength 74C are fixed at positions that are separated by at least the amplitude of the wavelength oscillation of the reflected light from the oscillation center 73C.

Furthermore, when the reflected light input distribution 73T is still, the slope 75T-1 on the lower side of the upper passband 75T crosses the slope 73-T on the upper side of the reflected light input distribution 73T, and the upper passband 75T and the reflected light input distribution 73T overlap with a width that is equal to or greater than the amplitude of the wavelength oscillation.

Similarly, when the reflected light input distribution is still, the slope 74T-1 on the upper side of the lower passband 74T crosses the slope 73T-2 on the lower side of the reflected input light distribution 73T, and the lower passband 74T and reflected light input distribution 73T overlap with a width that is equal to or greater than the amplitude of the wavelength oscillation.

By fixing the passband 75T and passband 74T with a position relationship with respect to the reflected light input distribution 73T as described above, it is possible to detect wavelength oscillation of the reflected light with high sensitivity.

The upper optical filter allows the reflected light corresponding to the portion where the reflected light input distribution 73T overlaps the passband 75T to pass, and outputs the reflected light. Similarly, the lower optical filter allows the reflected light corresponding to the portion where the reflected light input distribution 73T overlaps the passband 74T to pass, and outputs the reflected light.

Therefore, when the value of the wavelength of the reflected light increases and the reflected light input distribution 73T shifts upward, the output value of the upper optical filter having passband 75T increases, and the output value of the lower optical filter having passband 74T decreases. However, when the value of the wavelength of the reflected light decreases and the reflected light input distribution 73T shifts downward, the output value of the upper optical filter having passband 75T decreases, and the output value of the lower optical filter having passband 74T increases.

Consequently, when the change in the center wavelength of the reflected light oscillates due to the input wave 73W illustrated in FIG. 4A, the output value of the upper filter having passband 75T generates the output wave illustrated in FIG. 4C, and the lower optical filter having passband 74T generates the output wave 74W illustrated in FIG. 4C. As illustrated in FIG. 4C, the output wave 74W and output wave 75W have opposite phase wave motion.

According to the theory above, the spectrum analyzer 42 illustrated in FIG. 3 outputs lightwaves to the eight output ports P1 to P8 when oscillated, and these lightwaves are changed to electrical signals by the photoelectric converter 60 and outputted to the outside. The output from the spectrum analyzer 42 undergoes A/D conversion by an interface (not illustrated in the figure) and inputted to the arithmetic processing unit 50.

Figure 5:
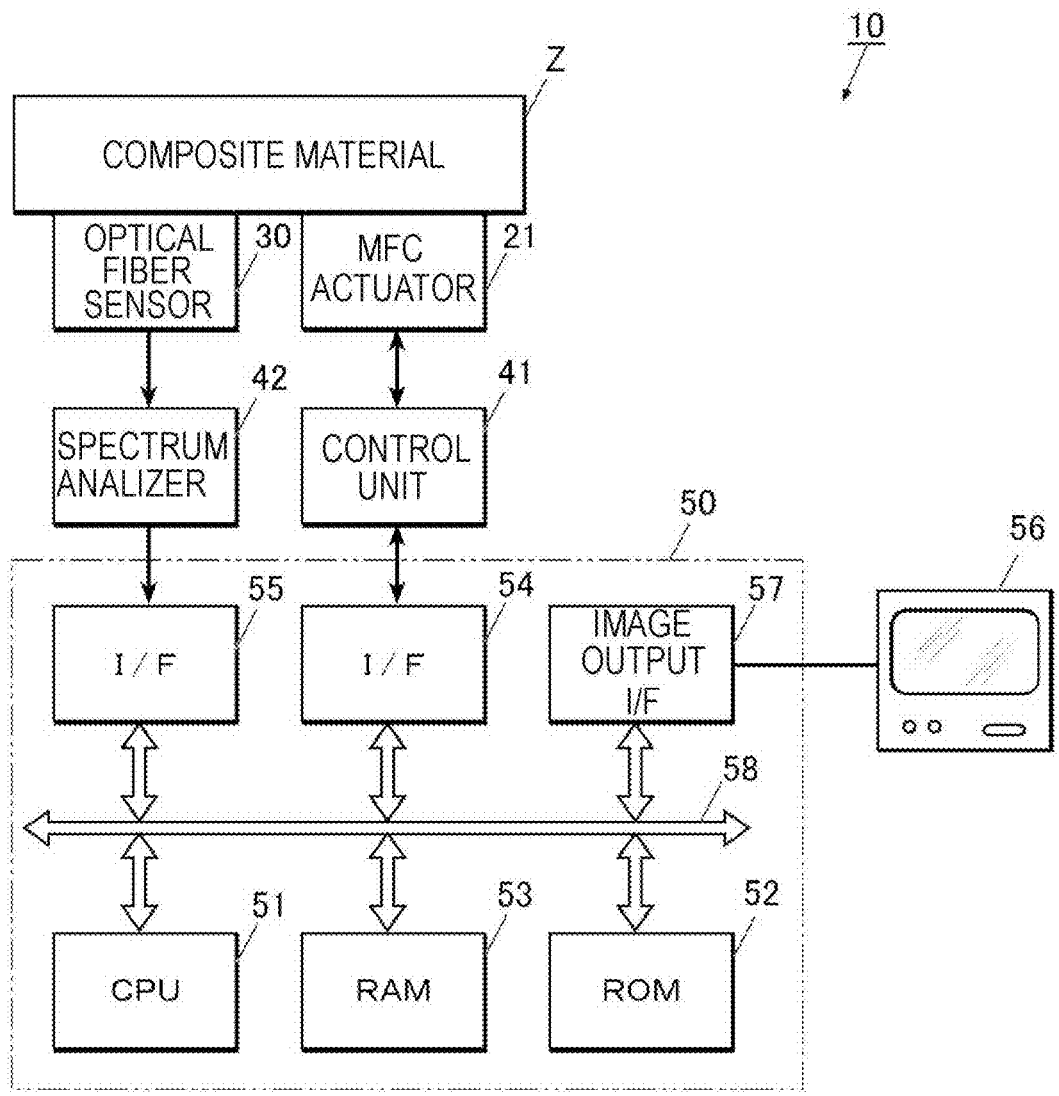
FIG. 5 is a block diagram illustrating the control system of a damage detection system of an embodiment of the present invention.

As illustrated in FIG. 5, the arithmetic processing unit 50 comprises a CPU 51 that performs arithmetic processing according to a program, ROM 52 that stores programs for performing various processing and control, RAM 53 that becomes a work area that temporarily stores data and the like for various processing, an interface 54 that makes it possible to transmit data to or receive data from the control unit 41, an interface 55 that inputs data from the spectrum analyzer 42, an image output interface 57 that converts the display data of the processing results to an image signal having a format that is suitable to the display 56, and outputs that signal to the display 56, and a data bus 58 that is used for transmitting various instructions or data between all of the components above.

The damage detection system 10, together with applying oscillation to a structural composite material Z, which is the object of damage detection, by way of the MFC actuator that is placed on the structural composite material, detects whether or not damage has occurred near the optical fiber sensors 30 according to the propagation state of the oscillation wave that is detected by the optical fiber sensors 30. In order to accomplish that, the arithmetic processing unit 50 executes various functions explained below by the CPU 51 using the RAM 53 to perform the processing of the various programs stored in the ROM 52.

The CPU 51, according to the programs stored in the ROM 52, controls the operation of the control unit 41 so that a driving voltage is applied to the MFC actuator 21. When there is a plurality of MFC actuators 21, any one of the actuators can be selected as the MFC actuator 21, however, when used as an oscillation source, for example, it is preferred that an MFC actuator be selected such that there is a portion between the optical fiber sensors 30 and the grating section 33 where damage to the structural composite material Z occurs easily.

The CPU 51, according to a program stored in the ROM 52, performs processing of applying a driving voltage, acquiring output wave data that is outputted in parallel from the spectrum analyzer 42 during the fixed period of oscillation caused by the MFC actuator 21, and storing the acquired data in the RAM 53.

Figure 7A:
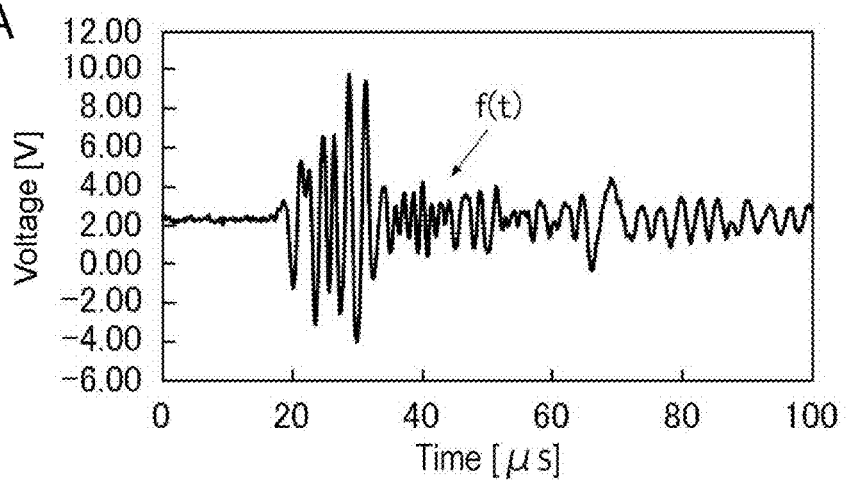
FIG. 7A is a detected wave that was detected by an FBG sensor related to testing.

The CPU 51, issues control instructions, and by way of the MFC actuator 21 applies the ultrasonic oscillation of a Lamb wave to the structural composite material Z, and quantifies and obtains the difference signal of the output wave 74W and the output wave 75W from the optical filter that is obtained during oscillation. For example, the difference signal f(t) illustrated in FIG. 7A is obtained.

Figure 7B:
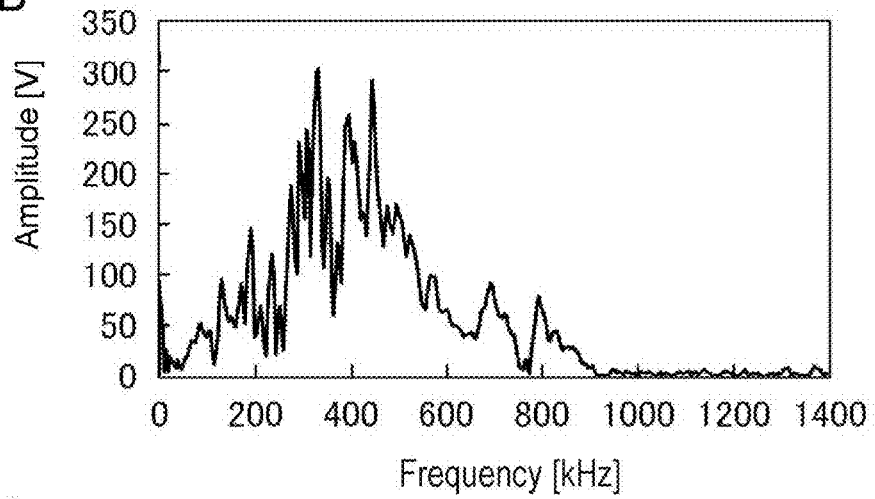
FIG. 7B is a Fourier spectrum of that FBG sensor.
Figure 7C:
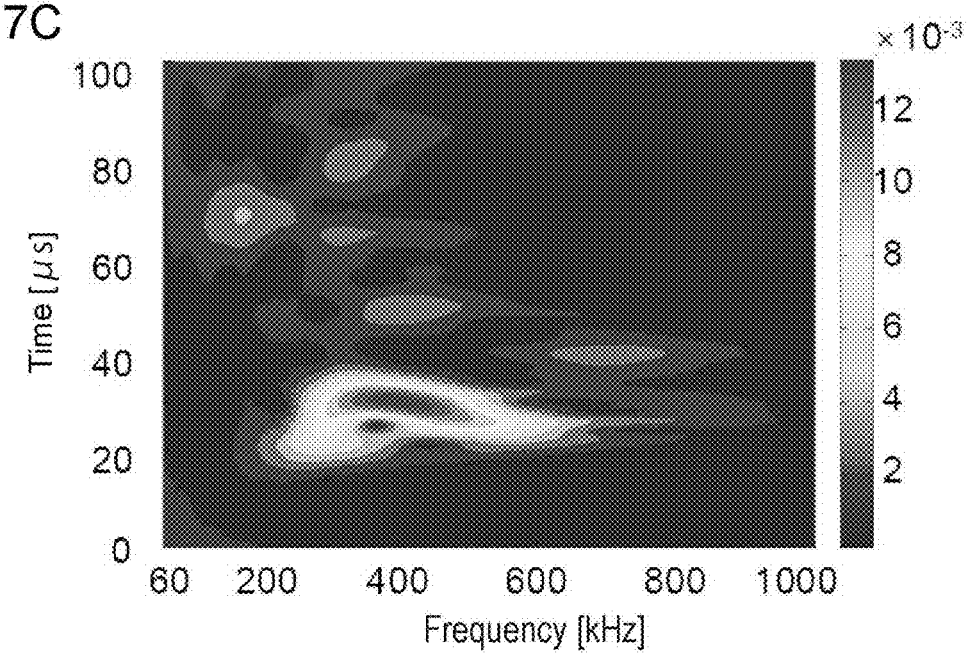
FIG. 7C is the wavelet transformation result.

The CPU 51 also performs wavelet conversion of the f(t) data according to Equation (2). As a result, the f(t) data is converted to propagation intensity distribution data that is expanded 2-dimensionally according to frequency and propagation time. This data corresponds to the propagation intensity distribution of the Lamb wave to the optical fiber sensors 30, and when represented graphically becomes as illustrated in FIG. 7C.

[Formula 2]

$$F(a,b) = \int_{-\infty}^{\infty} f(t) \psi^*_{a,b}(t) dt \quad (2)$$

[Damage Detection Operation]

Using the basic configuration explained above, and further as illustrated in FIG. 19 or FIG. 21, MFC actuators 21, 21 and optical fiber sensors 30, 30 are placed at the same positions on the top and bottom of the structural composite material Z, and the damage detection operation described below is executed.

Figure 11A:
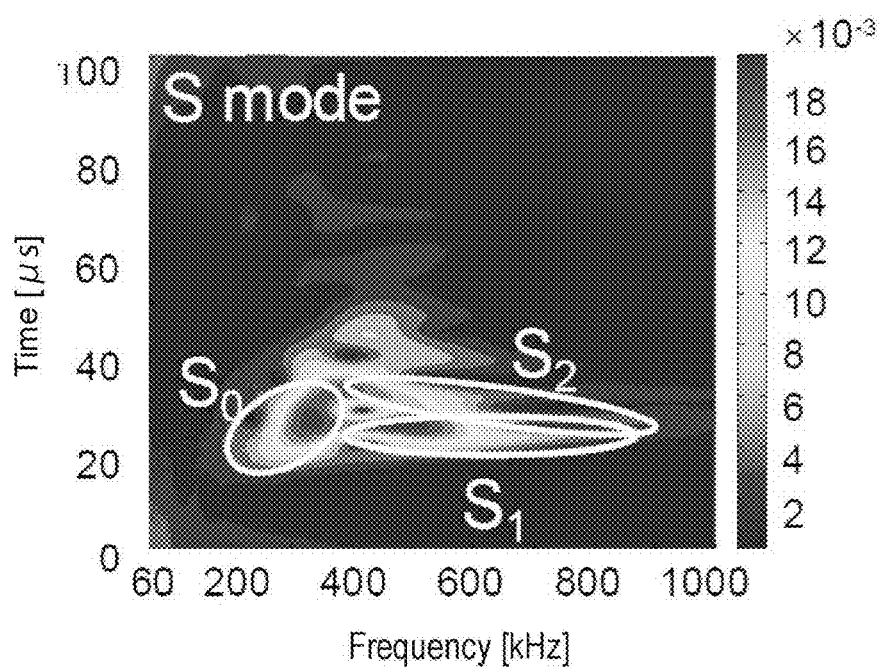
FIGS. 11A and 11B are diagrams illustrating mode identification results related to testing.
Figure 23:
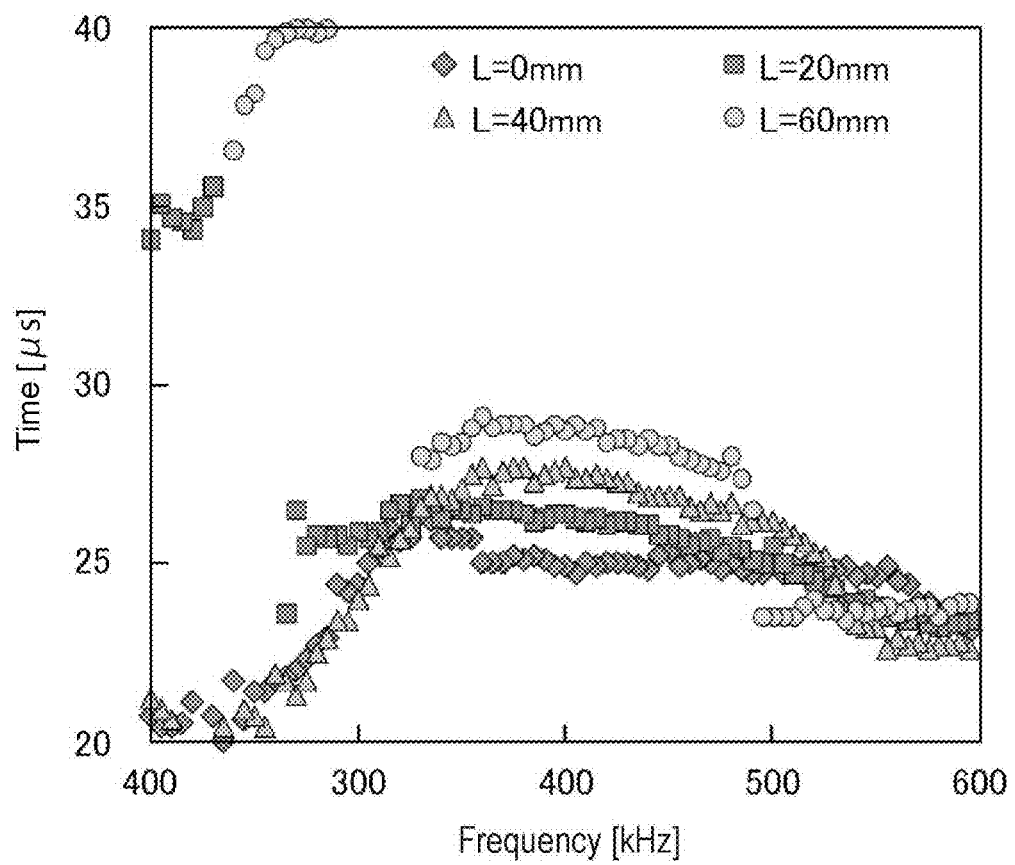
FIG. 23 is a diagram illustrating a plot of the time when the maximum wavelet coefficient occurred in the S0 and S1 modes at each frequency for each of the test specimens of different peeling lengths.

The CPU 51, by causing the top and bottom MFC actuators 21, 21 to generate an oscillating wave in the same phase, applies oscillation in just the symmetrical mode to the structural composite material Z, then performs wavelet conversion of the f(t) data as described above and obtains 2-dimensional expanded data according to the frequency and propagation time of just the S mode as illustrated in FIG. 11A. After that, the CPU 15, based on the theoretical dispersion curve illustrated in FIG. 8, specifies a mode, such as the S0 mode, S1 mode, S2 mode and the like, and calculates the propagation time where the maximum wavelet coefficient value occurs for each frequency in the specified mode. For example, when specified modes are the S0 mode and S1 mode, as illustrated in FIG. 23, the relationship between frequency and time at which the maximum wavelet coefficient value occurs is specified. This is one characteristic value and one measurement result that is extracted from the 2-dimensional expanded data. The CPU 51 displays this on the display 56 as illustrated in FIG. 23.

The CPU 51 displays the measurement results for a test object for which the damage state is unknown in the same way as and together with the measurement results for a structure for which the damage state is known. The tester references this, and through comparison, can estimate whether or not there is damage, and to what extent damage has occurred.

Figure 26:
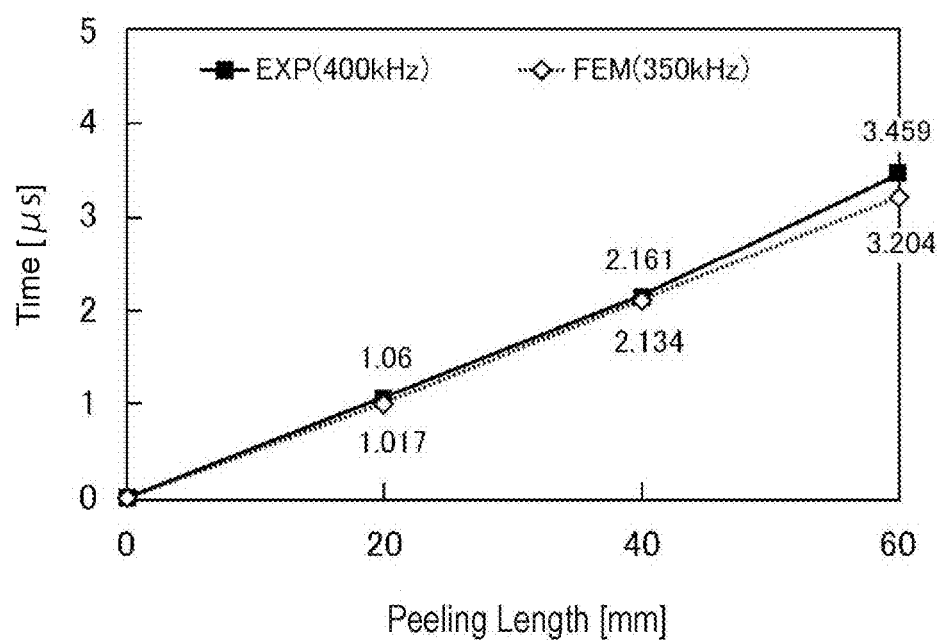
FIG. 26 is a graph illustrating the change in the amount of increase in propagation time in the S0 an S1 modes at 350 kHz (finite-element analysis) and at 400 kHz (testing) with respect to the peeling length.

Alternatively, the propagation time in the S0 mode and the S1 mode increases as the length of the lamination peeling increases, so, as illustrated in FIG. 26, the CPU 51 displays the amount of increased propagation time with respect to the case when there is no damage. The tester references this and can estimate whether or not there is damage, and to what extent damage has occurred.

The CPU 51 further advances, and based on the multiple measurement results stored in the ROM 52 for a structure for which the damage state is known, and the measurement results for a test object for which the damage state is not known, performs estimation of the extent of the damage that has occurred in the test object, and can display those results on the display 56.

In order to acquire data for the symmetrical mode (S mode), instead of the method above, by adding the output values of the top and bottom optical fiber sensors 30, 30, it is possible to obtain 2-dimensional data (propagation intensity distribution data) of which the asymmetrical mode is cancelled and the symmetrical mode is emphasized.

Figure 11B:
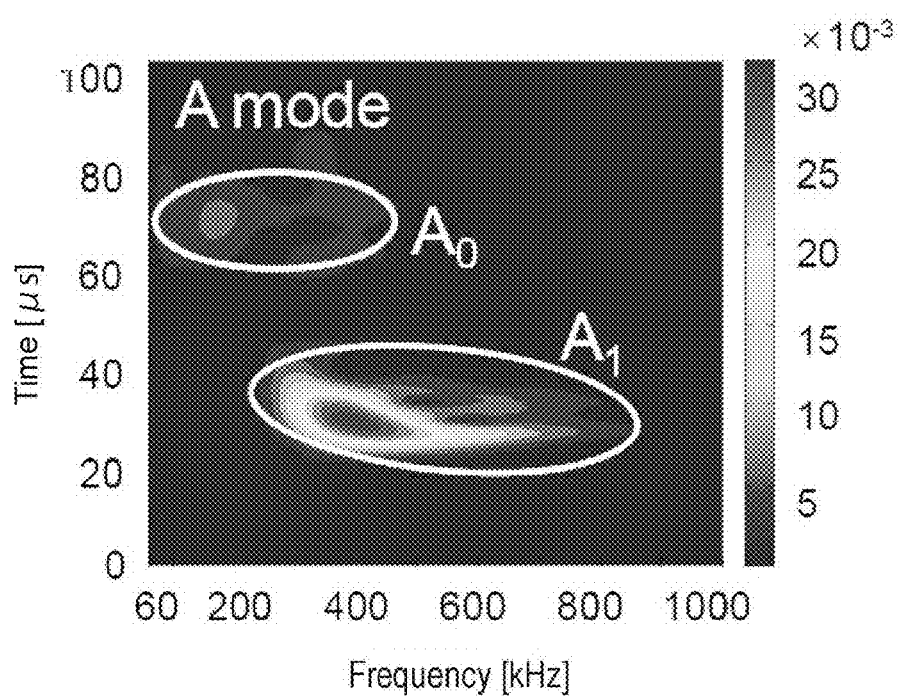
Figure 22:
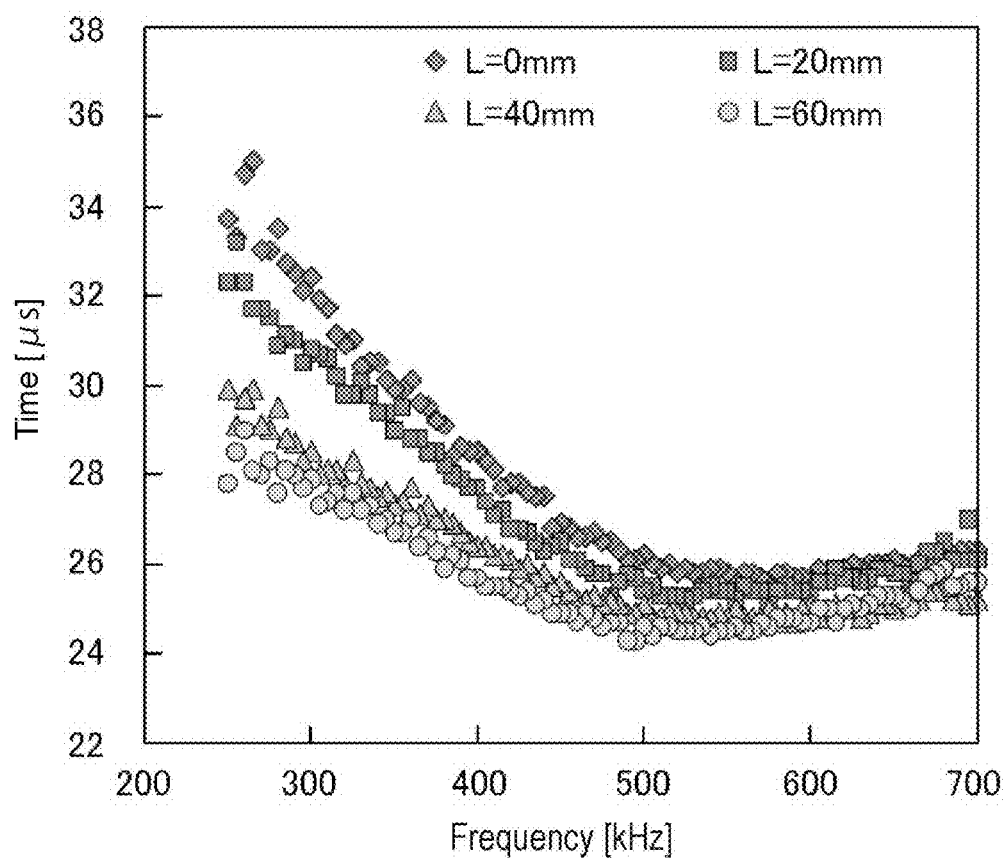
FIG. 22 is a diagram illustrating a plot of the time when the maximum wavelet coefficient occurred in the A1 mode at each frequency for each of the test specimens of different peeling lengths.

The CPU 51, by causing the top and bottom MFC actuators 21, 21 to generate an oscillating wave having opposite phase, applies just the asymmetrical mode to the structural composite material Z, performs wavelet conversion of the f(t) data as described above, and obtains 2-dimensional expanded data according to the frequency and propagation time of just the A mode as illustrated in FIG. 11B. After that, the CPU 51 specifies a mode such as the A0 mode and A1 mode, and calculates the propagation time at which the maximum wavelet coefficient value occurs for each frequency of the specified mode. For example, when the specified mode is the A1 mode, the relationship between the frequency and the propagation time at which the maximum wavelet coefficient value occurs as illustrated in FIG. 22 is specified. This is one characteristic value and one measurement result that is extracted from the 2-dimensional expanded data.

The CPU 51 displays this on the display 56 as illustrated in FIG. 22. The CPU 51 displays the measurement results for a test object for which the damage state is not know in the same way as and together with the measurement results for a structure for which the damage state is known. The tester references this, and by making a comparison, is able to estimate whether or not there is damage, and to what extent damage has occurred.

Alternatively, the propagation time in the A1 mode is reduced due to conversion to the S0 mode, which has a faster propagation time than the A1 mode in the damaged area, so the CPU 51 displays the amount of the reduction in propagation time with respect to the case in which there is not damage. The tester references this, and is able to estimate whether or not there is damage, and to what extent damage has occurred.

Moreover, the CPU 51 calculates the rate of change in the frequency with respect to the propagation time for the A1 mode. The approximation straight line of the measurement data sets of each test specimen in the 250 to 450 kHz range is calculated, and the rate of change corresponds to the slope of the approximation straight line. This also is one characteristic value and one measurement value that is extracted from 2-dimensional expanded data. The CPU 51 displays this rate of change (slope) numerically and in a graph as illustrated in FIG. 4. Here also, the CPU 51 displays measurement results for the test object for which the state of damage is unknown in the same way as and together with the measurement results for a structure for which the state of damage is known. The tester references this, and by making a comparison, is able to estimate whether or not there is damage, and to what extent damage has occurred.

Advancing further, based on the multiple measurement results stored in ROM 52 for a structure for which the damage state is known and measurement results for a test object for which the damage state is unknown, the CPU 51 performs estimation of the extent of data to the test object, and can display the results on the display 56. The basic data for estimation calculation is the amount of increase in propagation time in the S0 mode and S1 mode described above, and the amount of decrease and rate of change (slope) in the propagation time in the A1 mode.

In order to acquire data in the asymmetrical mode (A mode), instead of the method above, it is possible to obtain 2-dimensional expanded data (propagation intensity distribution data), in which the symmetrical mode is canceled out and the asymmetrical mode is emphasized, by subtracting the output values from the top and bottom optical fiber sensors 30, 30.

In the embodiment described above, the difference signal between the output values of two optical filters was taken to be the basic data for wavelet conversion, however, the invention is not limited to this, and the output value of one optical filter could be taken to be the basic data for wavelet conversion.

Moreover, in the embodiment above, the maximum peak value of the wavelet coefficient for a specified mode was calculated, however, the value of any parameter may be used as long as the parameter is suitable for use in comparing the acquired Lamb wave in specified modes.

Furthermore, in the embodiment described above, wavelet conversion was applied as the method of conversion for 2-dimensionally expanding the detected values from the optical sensors according to frequency and propagation time, however, the present invention is not limited to this, and it is also possible to apply other conversion methods such as short-time Fourier transformation, chirplet transformation, Wigner transformation, Stockwell transformation, or a combination of any two or more of said transformations.

[Verification Testing and Analysis]

Next, as a reference when explaining the theory of the present invention and when embodying the present invention, a description of verification performed through testing and analysis is given below.

1. MODE IDENTIFICATION METHOD (MODE SEPARATION METHOD)

Figure 6A:
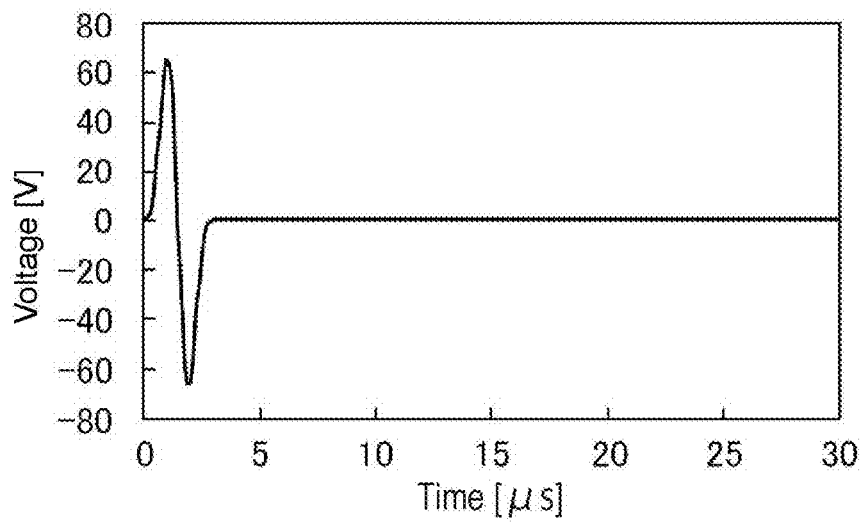
FIG. 6A is an input waveform of an FC actuator related to testing.
Figure 6B:
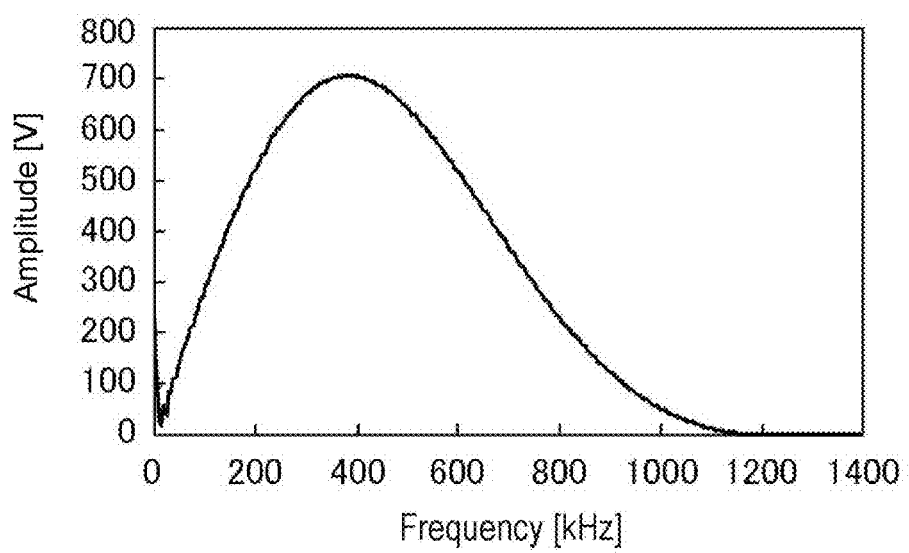
FIG. 6B is a Fourier spectrum of that FC actuator.

First, measurement was performed for a quasi-isotropic CFRP laminated plate (T700S/2500, Toray Industries Inc., [45/0/−45]3s, thickness: 3.4 mm). The MFC (M-2814-P2, Smart Material Co., Ltd.) had a length of 6 mm, width of 14 mm and thickness of 0.3 mm, and the FBG sensor (Fujikura, Ltd.) had a sensor length of 1.5 mm, and diameter with polyimide coating of 150 μm. Both were adhered to the surface of the CFRP laminated plate, being separated by 100 mm, and measurement was performed. Both were adhered to the surface using Aron Alpha (Konishi Co., Ltd.), which is a Cyanoacrylate type adhesive. A broadband signal with a hamming window in the first cycle of an fc=400 kHz sine wave as illustrated in FIG. 6 was used as the input signal to the MFC. In order to remove the noise from the received oscillation waveform of the Lamb wave, which is generated by the MFC, propagates through the laminated plate and is received by an FBG sensor, averaging was performed by waveforms measured 32,768 times. After that, signal analysis of the obtained received waveform was performed, and the mode dispersion characteristics that were included in the received oscillation wave were expressed in the time-frequency domain. A complex Morlet function was used as the window function in signal analysis, and 1D complex continuous wavelet analysis was performed. The waveform of the wave received by the FBG sensor, the Fourier spectrum of that waveform, and the wavelet conversion results are illustrated in FIG. 7. As a result, it could be confirmed that a wave component covering a broadband was received without a large peak appearing at the specified frequency. Moreover, from the wavelet conversion results, a plurality of modes having different speeds and frequencies were observed and found to have mode dispersion. Next, the theoretical dispersion curve for identifying each mode that appears in the received oscillation wave is derived.

Figure 8:
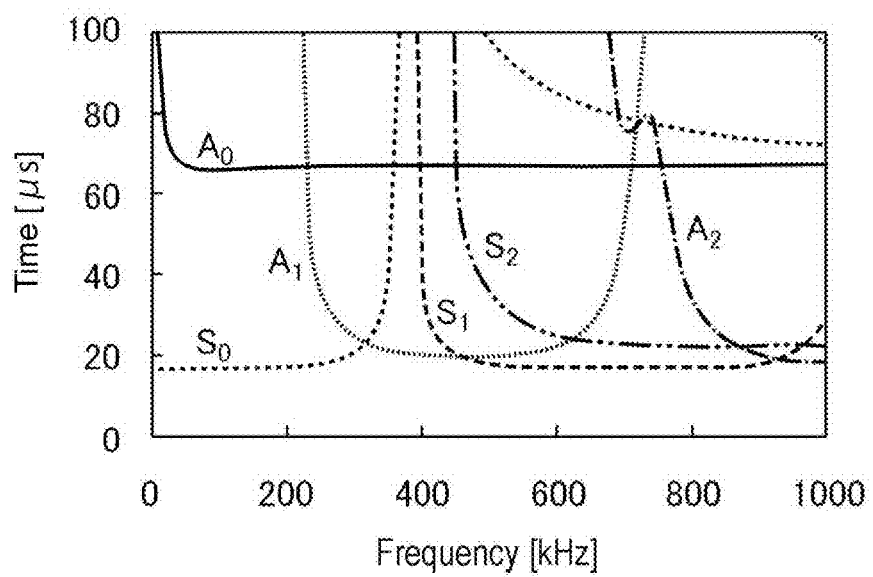
FIG. 8 is a theoretical dispersion curve of a Lamb wave under the same conditions as testing.

FIG. 8 illustrates the theoretical dispersion curve that was derived at the arrival time at a propagation distance of 100 mm in a 3.4 mm CFRP laminated plate that is the same as used in the testing above. In this dispersion curve, the arrival time of high-dimension modes suddenly becomes late, and where the frequency becomes infinitely large is called the cutoff frequency. By comparing this theoretical dispersion curve with the wavelet conversion results of the received oscillation waveform above, it can be seen that the mode dispersion coincides well between both. However, in the frequency domain of 300 kHz and greater where a plurality of modes overlap, it is difficult to identify the mode, so in order to perform accurate mode identification, it is necessary to separate these overlapping modes.

Figure 9:
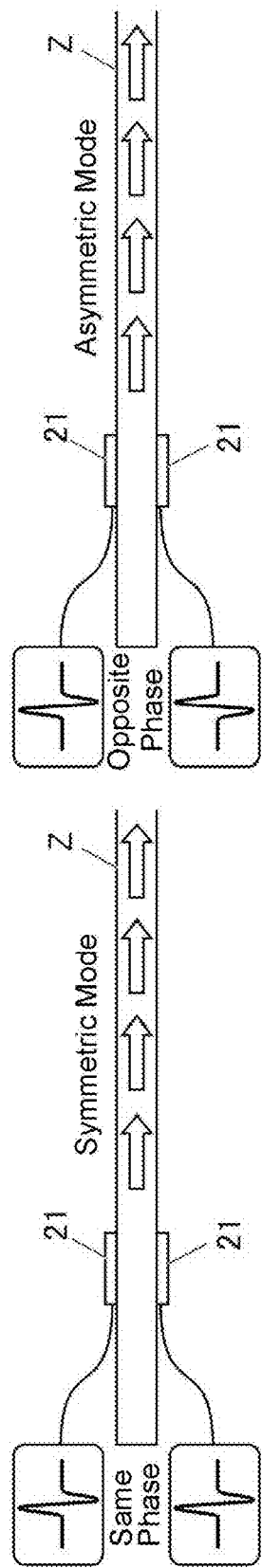
FIG. 9 is a concept diagram illustrating a mode separation method that uses an MFC actuator.

Therefore, a method of adhering both an MFC and FBG sensor at the same locations on the top and bottom surface of the laminated plate was used as a method for separating these modes. As illustrated in FIG. 9, an MFC is adhered at the same location on the top and bottom surface, and when the MFC generate waves that are in phase, it is possible to perform oscillation in just the symmetrical mode. On the other hand, when waves are generated having opposite phase, it is possible to perform oscillation in just the asymmetrical mode.

Figure 10:
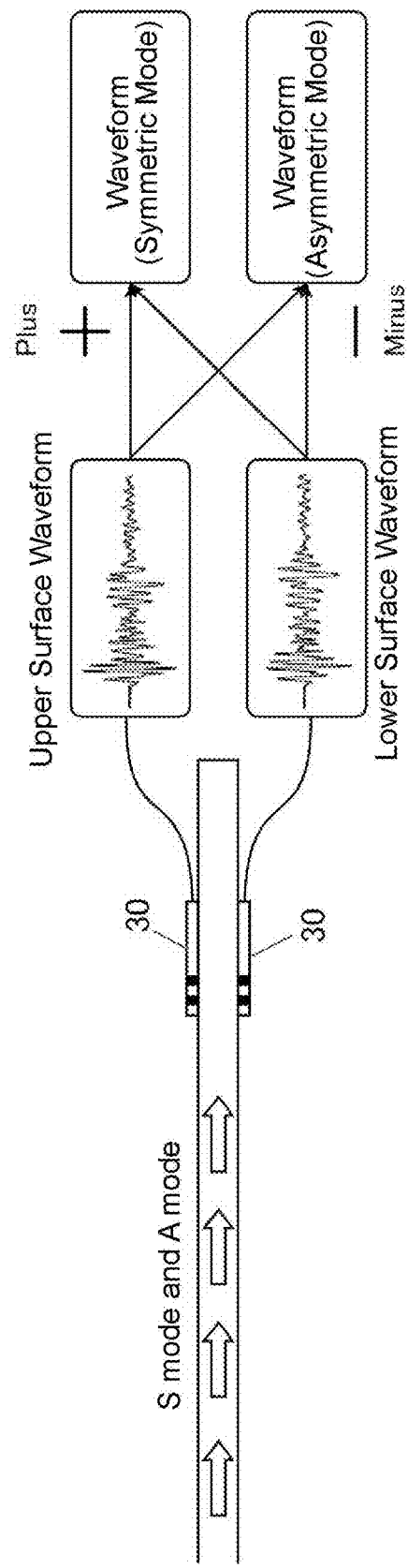
FIG. 10 is a concept diagram illustrating a mode separation method that uses an FBG sensor.

As illustrated in FIG. 10, an FBG sensor is adhered to the same position on both the top and bottom surface, and by taking the sum of the received oscillation waveform of the top and bottom of the plate, it is possible to separate the symmetrical modes, and by taking the difference, it is possible to separate the asymmetrical modes.

The result of using these two methods to separate the S (symmetrical) modes and A (asymmetrical) modes, perform wavelet conversion, and then perform comparison with the theoretical dispersion curve above is illustrated in FIG. 11. As a result, by separating the modes, overlapping of a plurality of modes is eliminated, and the modes could be identified accurately. It was also confirmed that in the received oscillation waveform there were the A0, S0, A1, S1 and S2 modes.

From the results above, it is possible to identify each mode included in a received Lamb wave by using the mode separation method above.

2. CAUSE OF CHANGE IN THE PROPAGATION TIME IN A SPECIFIED MODE (MODE CONVERSION BEHAVIOR IN A SECTION OF PEELING BETWEEN LAYERS)

In the previous section, identification of each mode was performed, and it became possible to understand the mode dispersion included in the measurement results. Next, the mode conversion behavior that occurs due to changes in the mode dispersion is clarified through testing and analysis.

(1) Mode Conversion Due to Changes in Sheet Thickness at Peeling Areas

Figure 12A:
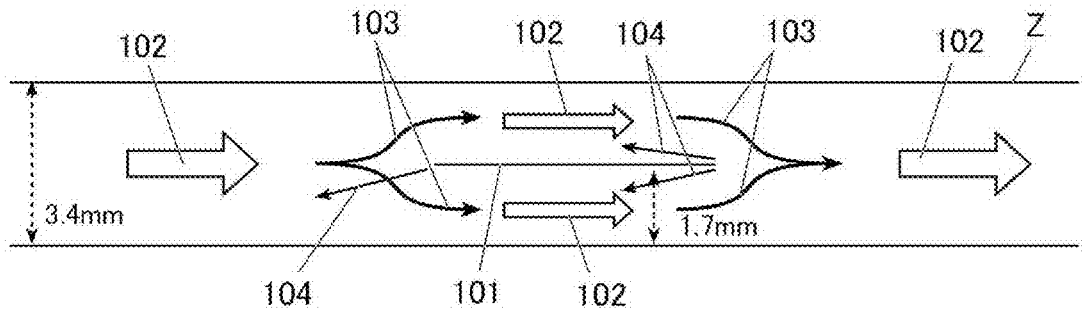
FIG. 12A is a concept diagram of the mode conversion behavior of a Lamb wave.
Figure 12B:
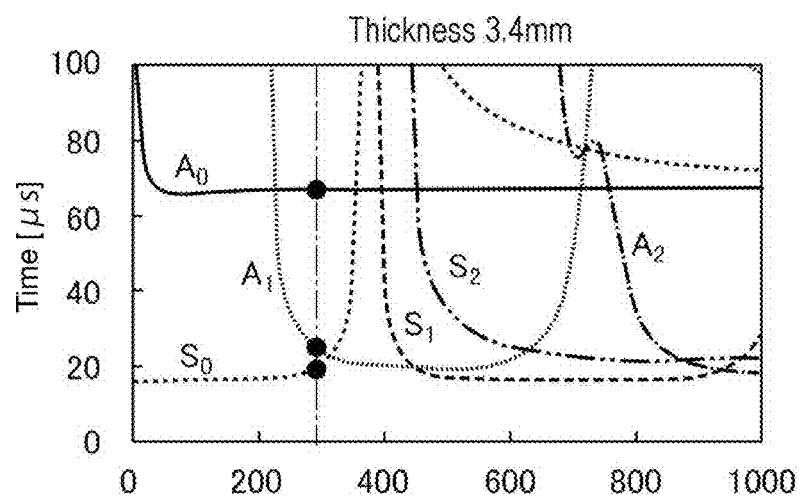
FIG. 12B is a theoretical dispersion curve of a Lamb wave that propagates inside a 2.4 mm thick plate.
Figure 12C:
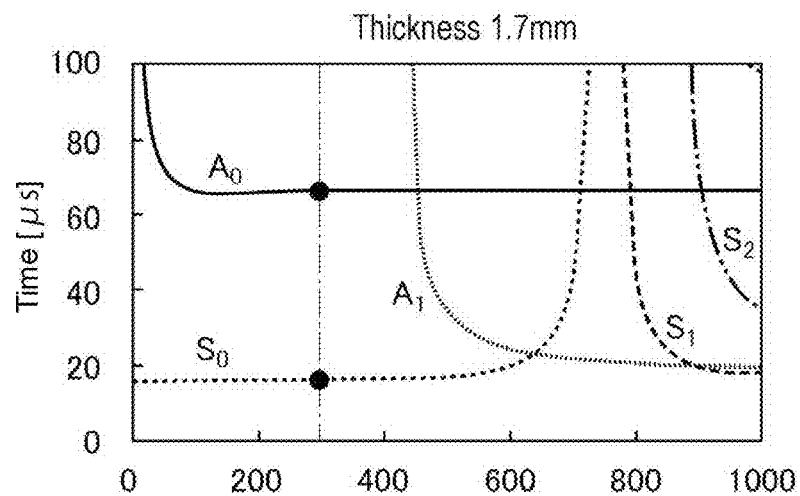
FIG. 12C is a theoretical dispersion curve of a Lamb wave that propagates inside a 1.7 mm thick plate.

The propagation speed of a Lamb wave depends on the product of the frequency and plate thickness, so as the plate thickness changes, the mode dispersion of a Lamb wave also changes. Therefore, as illustrated in FIGS. 12A to 12C, when peeling occurs between layers inside a laminated plate, the plate thickness of the propagation path at the area of peeling is less than in a healthy section, so the mode dispersion is different in healthy sections and peeling sections. Due to this change in mode dispersion, it is thought that mode conversion occurs in the Lamb wave that propagated through a healthy section, and propagates through a peeling section in a different mode form than in a healthy section.

For example, in a laminated plate having a plate thickness of 3.4 mm, there are three modes, A0, S0 and A1 modes, as the propagation form of a Lamb wave having a frequency of 300 kHz, however, when peeling occurs between layers in the center of the laminated plate, the plate thickness in the peeling section changes to 1.7 mm and there are only two propagation forms, the A0 mode and S0 mode.

Therefore, a Lamb wave that propagated though a healthy section as the A1 mode, undergoes mode conversion in the peeling section, and propagates as the A0 and S0 modes. However, which mode the wave will propagate by through the peeling section cannot be found from the theoretical dispersion curve. Therefore, the actual mode conversion behavior that occurs in peeling sections between layers is made clear by performing testing and finite-element analysis.

(2) Experiment

Figure 13:
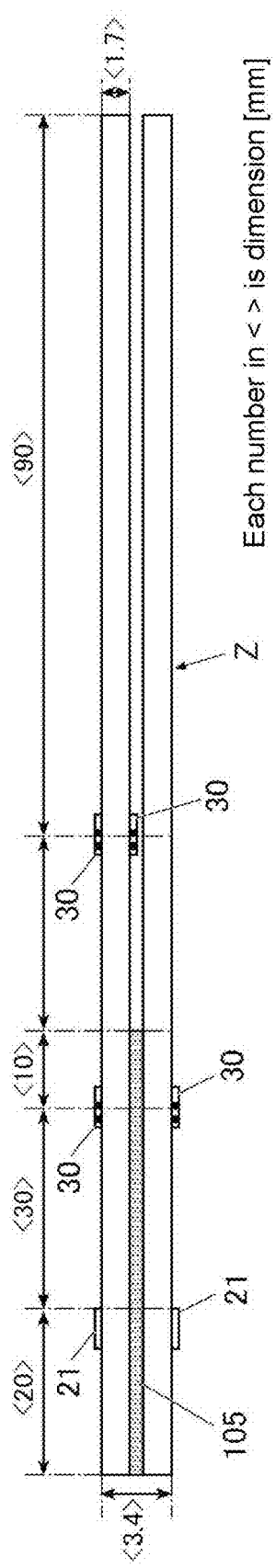
FIG. 13 is a cross-sectional diagram of a test specimen related to testing.

In order to make clear the actual mode conversion behavior that occurs at the beginning and ending of a peeling section between layers, a quasi-isotropic CFRP laminated plate (T700S/2500, Toray Industries Inc., [45/0/−45]3s, thickness: 3.4 mm) was used to simulate the case in which peeling between layers occurs in the center in the thickness direction of the plate. Mode identification of a received Lamb wave is performed by mode separation, so in order to measure the mode dispersion in a peeling section it is necessary to adhere an FBG sensor to the interior surface of the simulated peeling between layers. Therefore, two 1.7 mm thick CFRP laminated plates were prepared, and after an FBG sensor was adhered to one, and in order that the surface to which the FBG sensor was adhered was inside, an epoxy type adhesive, Araldite Standard (Huntsman Advanced Materials, Inc.) was applied in a 60 mm range from one end of the plate. The two CFRP laminated plates, in order to simulate a laminated structure [45/0/−45/90]3s, were made with a laminated structure [45/0/−45/90]3, and were symmetrically adhered to the mounting surface. The dimensions of the test specimen are illustrated in FIG. 13. The width of the plate is 90 mm.

The MFC (M-2814-P2) that was used had a length of 6 mm, a width of 14 mm and a thickness of 0.3 mm, and one was adhered to both the top and bottom surface of the laminated plate. FBG sensors were adhered to the top and bottom surface of the laminated plate at two points; a distance 30 mm from the tip end of the MFC where the plate thickness was 3.4 mm (healthy section), and at a distance 70 mm where the plate thickness was 1.7 mm (peeling section), and these sensors received the Lamb wave. The FBG sensors (Fujikura Ltd.) that were used in testing had a sensor length 1.5 mm, and diameter with polyimide coating of 150 µm. Aron Alpha (Konishi Co., Ltd.) was used for adhering the elements. The input signal was a fc=400 kHz sine wave with a hamming window in one cycle, and in order to remove noise from the received oscillation waveform, averaging was performed by waveforms measured 32,768 times. The mode conversion behavior of the S mode that was found by performing oscillation in just the S (symmetrical) mode using the MFC on both the top and bottom surfaces is illustrated in FIG. 14, and the mode conversion behavior of the A mode that was found by performing oscillation in just the A (asymmetrical) mode is illustrated in FIG. 15.

Figure 14:
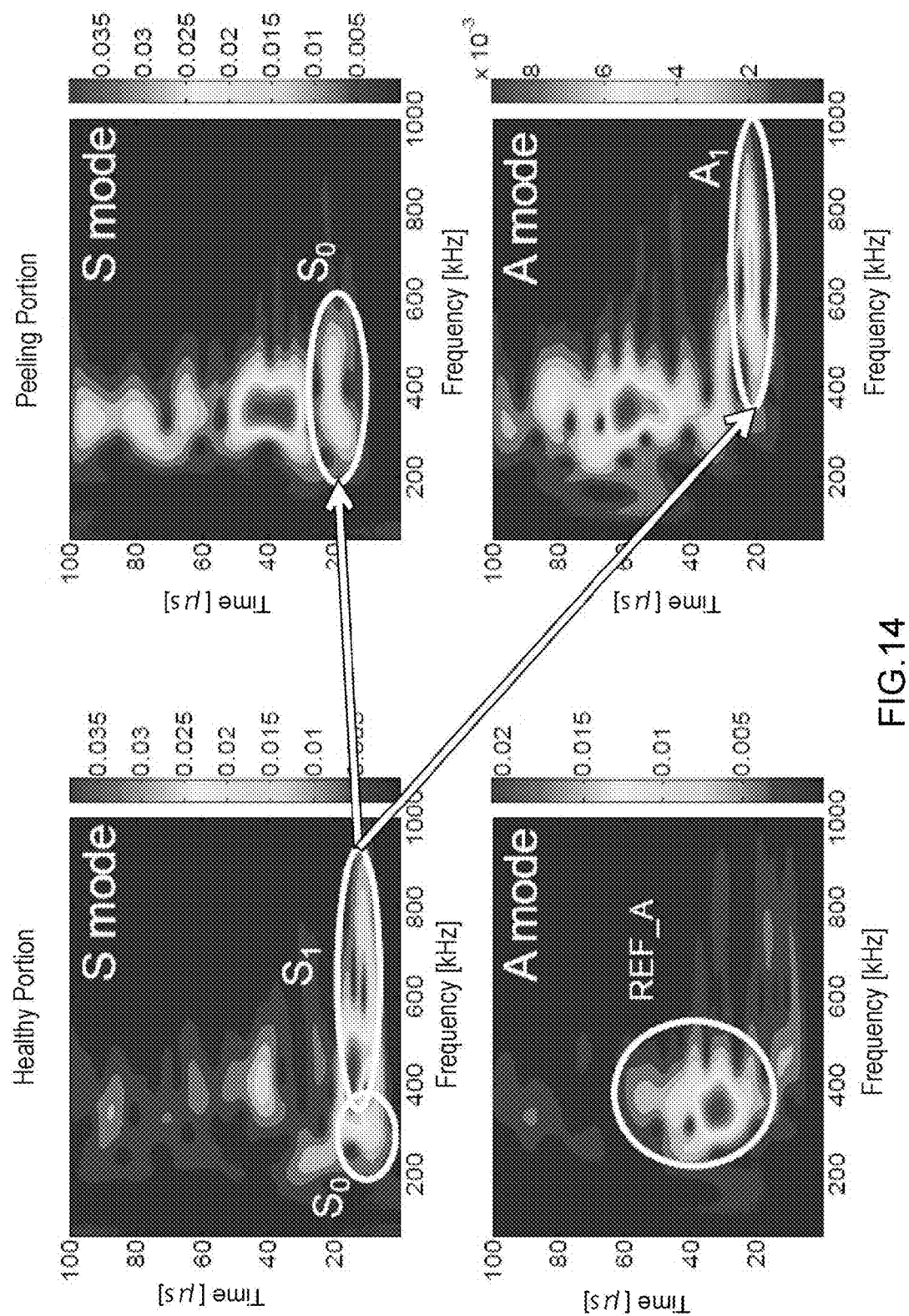
FIG. 14 is a diagram illustrating the mode conversion behavior of the S mode found from testing.

From the results in FIG. 14, in the case of generating oscillation in only the S mode, only the S0 mode and S1 mode were observed in the healthy section. From the theoretical dispersion curve in the case of the 1.7 mm plate thickness illustrated in FIG. 12C, it is seen that in the peeling section, the S1 mode only existed at 800 kHz or greater, so it is thought that in the healthy section, the S1 mode undergoes mode conversion in the peeling section and the wave propagates as another mode. Therefore, observing the modes that exist in the peeling section, two modes, the S0 mode and A1 mode, were observed. From this result, at the start of the peeling section, it was confirmed that "S1 mode→S0 mode→A1 mode" mode conversion occurred.

Figure 15:
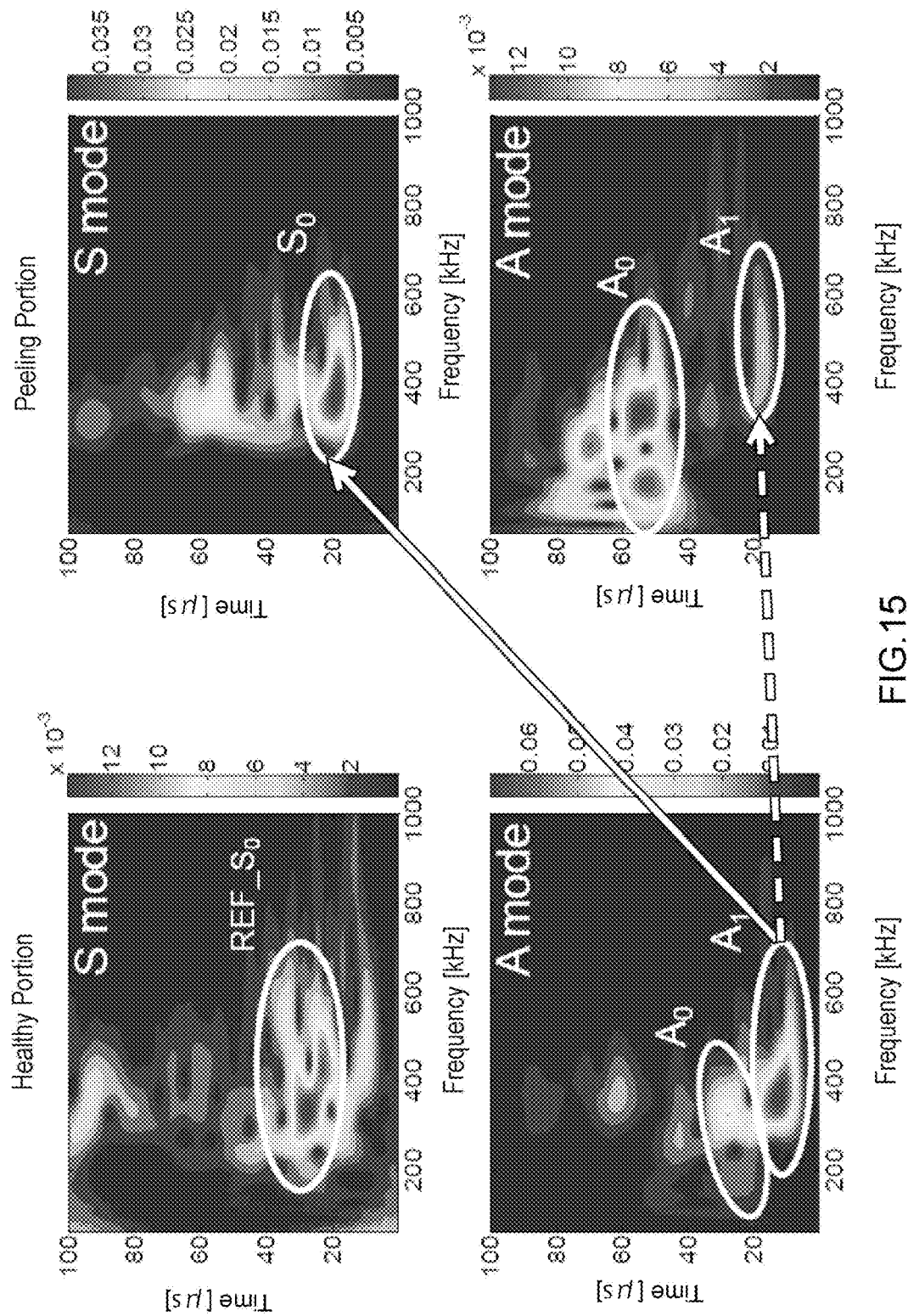
FIG. 15 is a diagram illustrating the mode conversion behavior of the A mode found from testing.

From the results in FIG. 15, when oscillation was generated in only the A mode, only the A0 mode and A1 mode were observed in the healthy section. From the theoretical dispersion curve in the case of a 1.7 mm plate thickness illustrated in FIG. 12C, it was seen that in the peeling section, the A1 mode existed at only 500 kHz or greater, so it is thought that the A1 mode that was observed in the healthy section undergoes mode conversion in the peeling section and that the wave propagates as another mode. Therefore, observing the modes that exist in the peeling section, two modes, the S0 mode and A1 mode are observed (the arrival time of the A0 mode is late, so is not considered to be an object of mode conversion). In this peeling section, it is thought that the observed A1 mode does not undergo mode conversion, but that at 500 kHz or greater, the A1 mode propagates as is. Therefore, from this result, at the start of the peeling section, it was confirmed that "A1 mode→S0 mode" mode conversion occurred.

(3) Verification by Finite-Element Analysis

Figure 16:
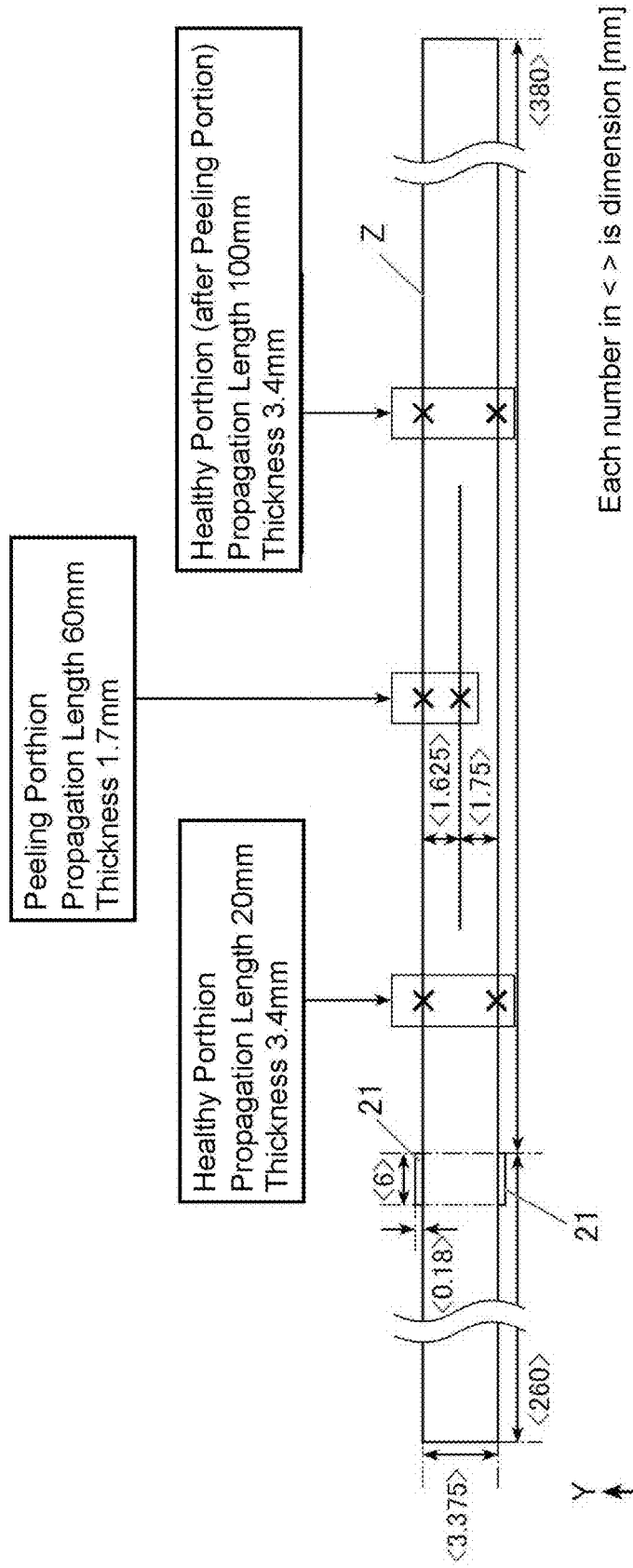
FIG. 16 is a cross-sectional diagram of a finite-element analysis model.

In order to verify the mode conversion behavior found from observation in (2) above, 2D finite-element analysis was performed. The finite-element model and dimensions are illustrated in FIG. 16. An LS-DYNA 971 was used for the model construction and analysis. The elements used for the analysis model were 2D shell elements (plane strain). The mesh size was 0.125 mm, which was sufficiently small enough to be able to calculate high-frequency waves with a short wavelength. Node bonding is performed for the contact sections between the MFC and CFRP laminated plate, and as in testing, a sine wave having a frequency of 400 kHz and a hamming winding in 1 cycle was used as the input waveform to the MFC. With the LS-DYNA it is not possible to calculate the piezoelectric effect, so the piezoelectric effect was applied as the coefficient of thermal expansion in the direction of expansion of the MFC and simulated. Under the conditions described above, the time history of the strain in the x direction was calculated at the three oscillation receiving points illustrated in FIG. 16 (healthy section: 20 mm propagation distance 20, 3.4 mm plate thickness; peeling section: 60 mm propagation distance, 1.7 mm plate thickness; and healthy section (after passing the peeling section): 100 mm propagation distance, 3.4 mm plate thickness), and this was taken to be the received oscillation waveform. The mode conversion behavior in the S mode that was found by performing oscillation in only the S (symmetrical) mode using both the top and bottom MFC is illustrated in FIG. 17, and the mode conversion behavior in the A mode that was found by performing oscillation in only the A (asymmetrical) mode is illustrated in FIG. 18.

Figure 17:
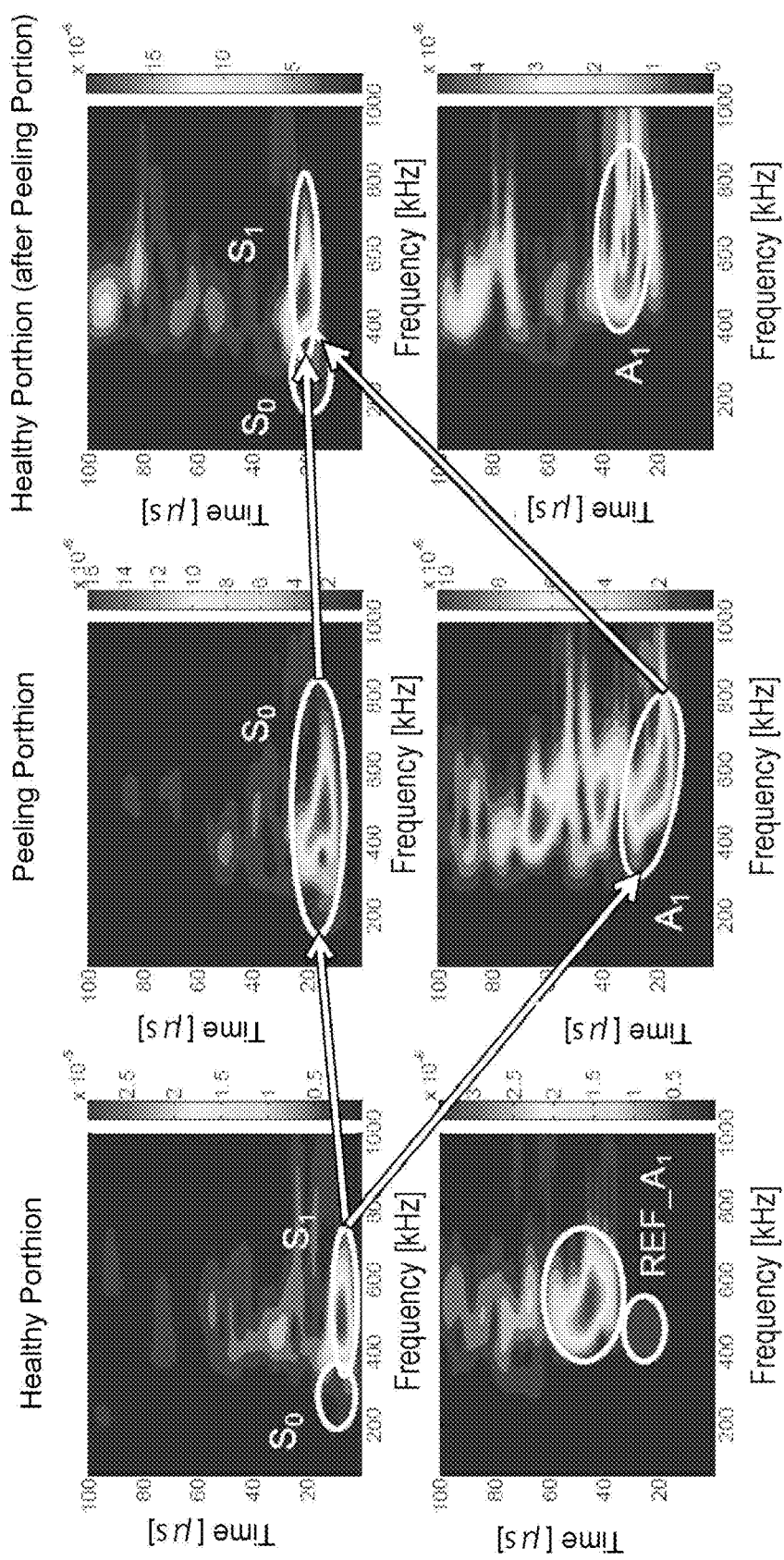
FIG. 17 is a diagram illustrating the mode conversion behavior of the S mode found from finite-element analysis.

From the results in FIG. 17, at the start of peeling between layers, it was confirmed that the same "S1 mode→S0 mode→A1 mode" mode conversion as in the testing occurred. Moreover, in the healthy section after passing the peeling between layers, the same dispersion as in the healthy section before passing the peeling was observed, and the S0 mode and S1 mode were observed. When this S1 mode propagated through the peeling section and returned to the healthy section, it is thought that the S0 mode and A1 mode of the peeling were converted again to the S1 mode in the healthy section.

Figure 18:
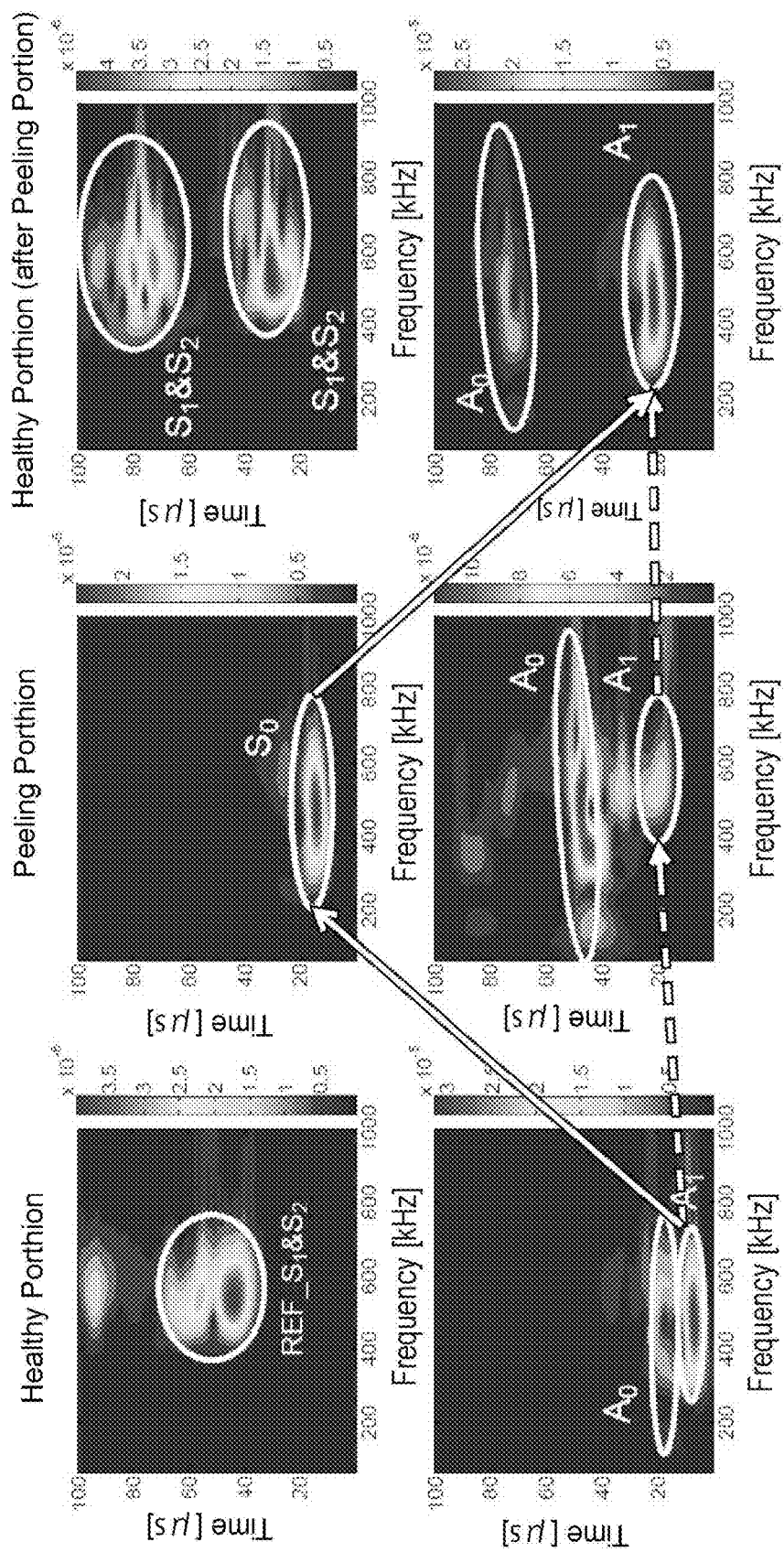
FIG. 18 is a diagram illustrating the mode conversion behavior of the A mode found from finite-element analysis.

Next, from the results in FIG. 18, it was confirmed that at the start of the peeling between layers, there was the same "A1 mode→S0 mode" mode conversion as in testing. Moreover, in the healthy section after passing the peeling between layers, the same dispersion as in the healthy section before passing the peeling was observed, and the A0 mode and A1 mode were observed.

When this A1 mode propagates through the peeling section and returns to the healthy section, it is thought that the S0 mode in the peeling section undergoes mode conversion and is converted again to the A1 mode in the healthy section.

The above indicates the validity of the mode conversion behavior found through testing, and further makes clear the mode conversion behavior that occurs after the peeling between layers ends. As a result, it was confirmed that when passing through the peeling section between layers, the following two mode conversions exist.

"S1 mode→S0 mode, A1 mode→S1 mode"
"A1 mode→S0 mode→A1 mode"

Figure 19A:
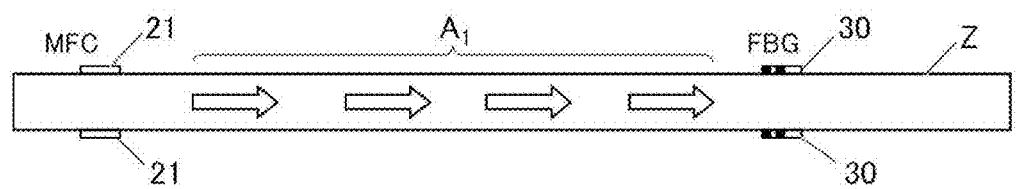
FIGS. 19A and 19B are diagrams illustrating the difference in propagation states, where
Figure 19B:
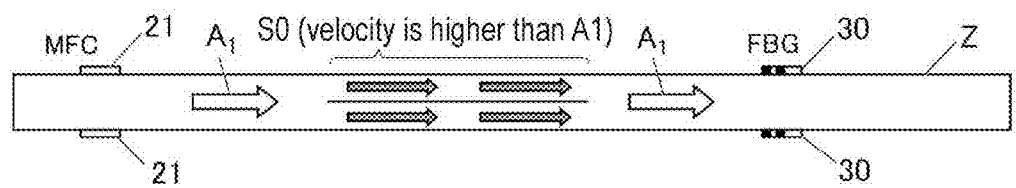

Due to this kind of mode conversion behavior, the mode during propagation through a peeling section and the mode during propagation though a healthy section differ. For example, as illustrated in FIG. 19, in the "A1 mode→S0 mode→A1 mode" mode conversion, in the healthy sections, propagation in all propagation paths is in the A1 mode, however, when peeling occurs, propagation through that area is in the S0 mode. Here, the propagation speeds in the A1 mode in healthy sections (3.4 mm plate thickness) and in the S0 mode in peeling section (1.7 mm plate thickness) differ, with the speed of the S0 mode being faster than that of the A1 mode. Therefore, the arrival time of oscillation in the A1 mode that is received by the FBG sensor is earlier when peeling has occurred than when healthy. This change in the arrival time occurs due to the difference in propagation speeds of a mode propagating though healthy sections and a mode propagating through peeling sections, and the length of the peeling. Therefore, by taking this difference as an index, it is possible to detect peeling between layers, and to quantitatively evaluate the peeling length.

3. VERIFICATION TESTING AND ANALYSIS OF DETECTION OF ARTIFICIAL PEELING BETWEEN LAYERS (1) Verification Testing The effectiveness of the present invention is illustrated by verifying through testing whether or not there is actually a change in arrival time of a wave after passing through a peeling section.

Figure 21:
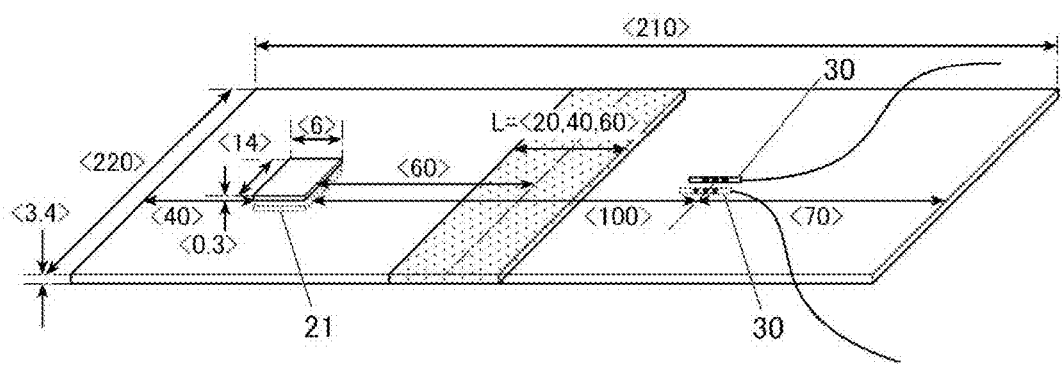
FIG. 21 is a perspective diagram of a section of a measured object that is related to detection testing of peeling between artificial layers.

Therefore, three kinds of laminated plates were made in which, while forming an isotropic laminated plate such as a quasi-isotropic CFRP laminated plate, peeling, having peeling lengths L=20, 40 and 60 mm, was artificially introduced between layers in the center in the plate thickness direction by embedding two layers of 50 μm thick Teflon (registered trademark) film between adjacent 90° layers in the center in the plate thickness direction. A broadband Lamb wave was caused to propagate such that it passed through these peeling areas, and the received oscillation waveform was measured. The testing configuration is illustrated in FIG. 21. An MFC and FBG sensor were adhered to the same locations on the top and bottom surfaces of the plate, and mode separation was performed in the same way as was performed in the case of clarifying the mode conversion behavior in the previous section.

Using this testing configuration, detection of peeling between artificial layers was tested using a laminated plate in which artificial peeling, having lengths L=20, 40 and 60 mm, was introduced. The results of this testing were compared with the results when a healthy laminated plate (L=0) was measured, and the change in the arrival time was evaluated.

In order to do this, after the received oscillation waveform underwent wavelet conversion, the maximum value of the wavelet coefficients for each frequency was extracted. When there was peeling between layers, the amount of change in the time of this maximum wavelet coefficient from the healthy state corresponds to the change in arrival time.

When oscillation was generated in the A mode using the MFC on both the top and bottom, the "time at which the maximum wavelet coefficient appeared for each frequency" in the A mode that was measured by the FBG sensors is illustrated in FIG. 22 for the 200 to 700 kHz A1 mode in which relatively large change occurred in the arrival time for the cases of L=0, 20, 40 and 60 mm.

Next, when oscillation was generated in the S mode using the MFC on both the top and bottom, the "time at which the maximum wavelet coefficient appeared for each frequency" in the S mode that was measured by the FBG sensors is illustrated in FIG. 23 for the 400 to 600 kHz S0 and S1 modes in which relatively large change occurred in the arrival time for the cases of L=0, 20, 40 and 60 mm.

Figure 20:
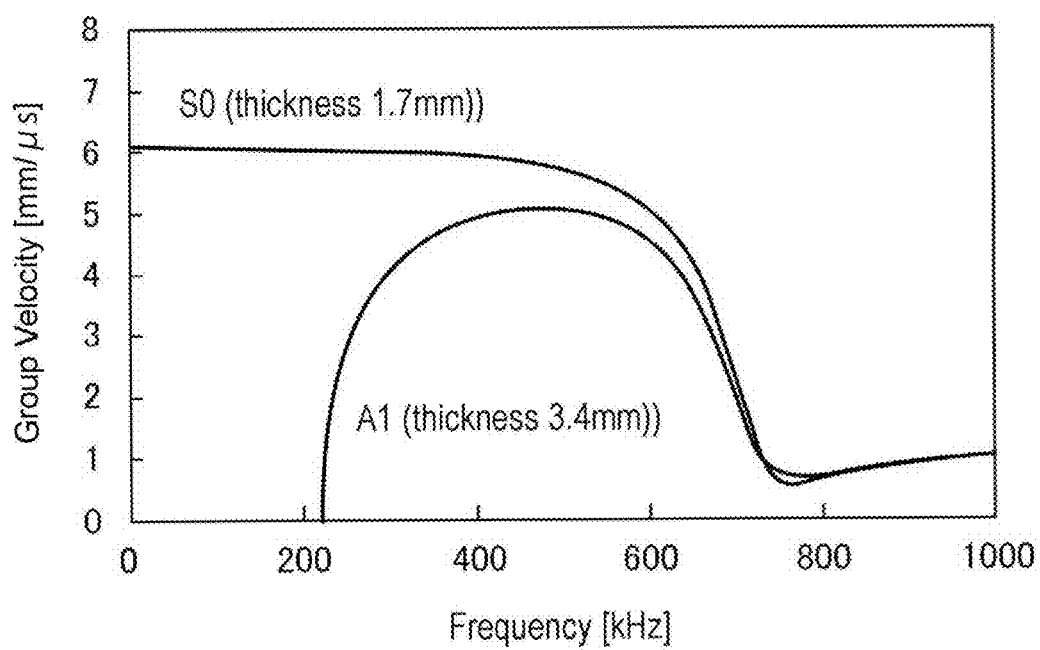
FIG. 20 is a diagram illustrating the difference between the speed in the A1 mode in a healthy section and in the S0 mode in a peeling section.

From FIG. 22 it is observed that as the peeling length becomes longer, the arrival time of the A1 mode becomes earlier. It is also observed that there is change in the slope of the mode dispersion in the 200 to 500 kHz frequency range. As illustrated in FIG. 20, this means that the closer the frequency is to the cutoff frequency of the A1 mode (frequency become low), the greater the difference between the propagation speed of the S0 mode and A1 mode becomes.

Moreover, from FIG. 23 it is observed that as the peeling length becomes long, the arrival time of the S0 and S1 modes becomes later.

The results above, show that there is indeed change in the arrival time when peeling between layers occurs, and that the present invention is effective.

(2) Verification Through Finite-Element Analysis

In section 2.(3) above, the peeling length of a 2D finite-element analysis model was changed as L=20, 40 and 60 mm, and analysis was performed using the same testing configuration as in the testing above. After that, as in the testing, the maximum amplitude was found for the A1 mode and S0 and S1 modes, and in observing the change in the arrival time, the results of the testing (FIG. 22, FIG. 23) coincide and the same change was observed.

(3) Quantitative Evaluation of the Peeling Length

Furthermore, using the change in the arrival time that was observed from test results in (1) above and from the analysis results in (2) above, or the slope of the mode dispersion as an index, it is shown that it is possible to quantitatively evaluate the peeling length.

A linearly approximated straight line is calculated from a plot of maximum amplitude values in the frequency ranges where change occurred in the arrival time, and using that approximated straight line, the following indices were found. The indices were found from test results and analysis results. The results of plotting the indices for each peeling length are illustrated in FIG. 24, FIG. 25 and FIG. 26.

Figure 24:
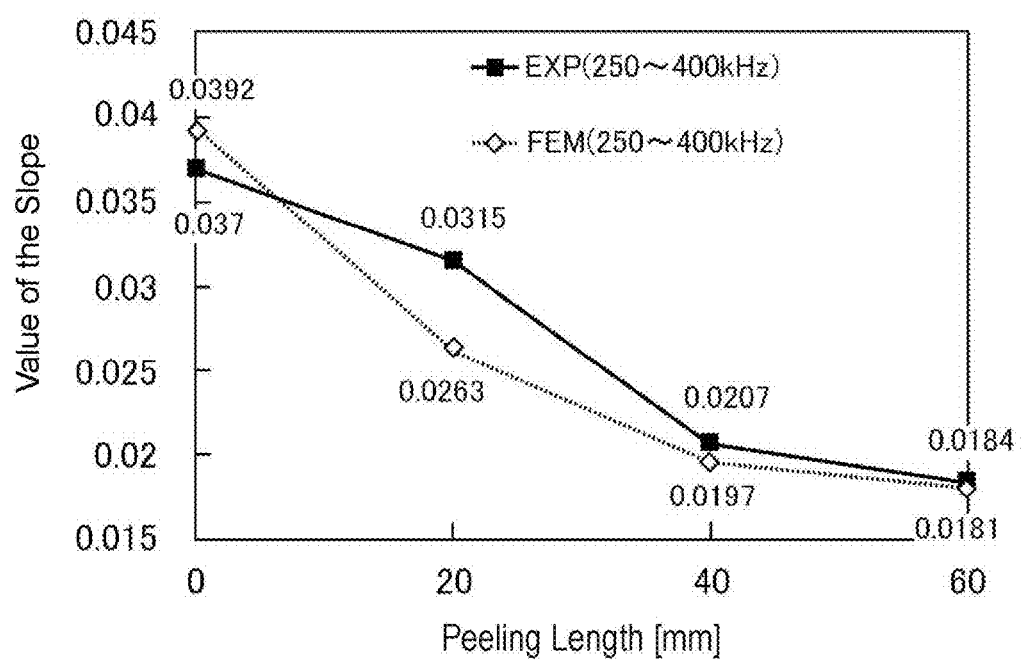
FIG. 24 is a graph illustrating the change in the slope of the approximation straight line of the measurement data group for each test specimen in the 250 to 400 kHz range in FIG. 22 with respect to the peeling length.
Figure 25:
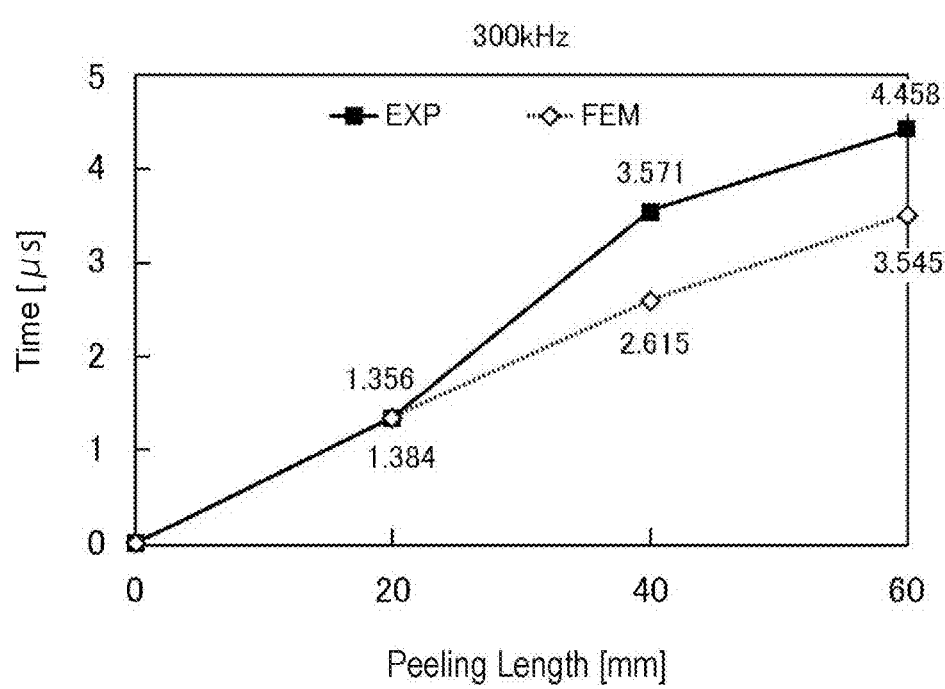
FIG. 25 is a graph illustrating the change in the amount of decrease in propagation time in the A1 mode at 300 kHz with respect to the peeling length.

FIG. 24 illustrates the slope of the mode dispersion of the 250 to 400 kHz A1 mode, FIG. 25 illustrates the amount of decrease in the arrival time of the A1 mode at 300 kHz, and FIG. 26 illustrates the amount of increase in the arrival time of the S0 and S1 modes at 400 kHz (analysis was at 350 kHz).

From the results in FIG. 24, it is observed that as the peeling length becomes longer, the slope of the mode dispersion becomes smaller. Also, from the results of FIG. 25 and FIG. 26, it is observed that as the peeling length becomes larger, the amount of decrease in the arrival time of the A1 mode, and the amount of increase in the arrival time of the S0 and S1 modes becomes greater. These indices change nearly proportional to the peeling length. Therefore, it is possible to use these indices to quantitatively evaluate the peeling length.

4. CONCLUSION

As described above, first, identification was performed of each mode of a broadband Lamb wave that is measured in a broadband ultrasonic transmission system. A method of separating symmetrical/asymmetrical modes is proposed as a method for doing this, and it was shown that mode identification is possible by using this separation method.

Next, the mode conversion behavior in peeling sections between layers was clarified through testing and analysis, and it was confirmed that there are two types of mode conversion behavior, "S1 mode→S0 mode, A1 mode→S1 mode" and "A1 mode→S0 mode→A1 mode".

After that, the validity of the peeling detection method of the present invention, which uses the change in speed of a Lamb wave due to mode conversion, was verified through testing and analysis. As a result, it was confirmed that the change in speed in the peeling sections was observed as the change in arrival time.

Finally, it was shown that the peeling length could be quantitatively evaluated using the slope of the mode dispersion in the A1 mode, the amount of decrease in the arrival time of the A1 mode and the increase in the arrival time of the S0 and S1 modes as indices.

It is to be understood that the above-described embodiments are illustrative of only a few of the many possible specific embodiments which can represent applications of the principles of the invention. Numerous and varied other arrangements can be readily devised by those skilled in the art without departing from the spirit and scope of the invention.

What is claimed is:

1. A system for damage diagnosis for diagnosing damage on or within an object constructed of a Carbon Fiber Reinforced Plastic (CFRP) material, the system comprising:

two oscillators, each oscillator comprising an MFC (Macro Fiber Composite) actuator having a piezoelectric element, with one oscillator being attached to one surface, and the other oscillator being attached to a second, opposing surface in the thickness direction of the object, for applying a broadband ultrasonic oscillation to the object to generate in the object a broadband Lamb wave comprising at least a one-dimensional asymmetric (A1) mode by causing strain orthogonal to an axial direction of the piezoelectric element, which is a direction parallel to a direction of wave propagation;

an oscillation detection sensor comprising an FBG (Fiber Bragg Grating) optical fiber placed near a location of the damage diagnoses, for detecting the broadband Lamb wave propagating through the object by detecting strain occurring in an axial direction of the FBG optical fiber;

a spectrum analyzer, connected to the oscillation detection sensor, comprising a light source that includes all oscillation areas of reflected wavelengths of the oscillation detection sensor; and a processing unit, being connected to the oscillator, the spectrum analyzer, and the oscillation detection sensor, and having processes for (1) executing an oscillation control process to control the oscillators, wherein the processing unit controls the two oscillators so that an asymmetrical mode Lamb wave having directivity, is generated in the object, (2) obtaining, via output wave data acquired from the spectrum analyzer, a two-dimensional propagation intensity distribution of the broadband Lamb wave according to propagation time and frequency based on a time-frequency transformation, (3) analyzing a portion of the two-dimensional propagation intensity distribution, the portion indicating the propagation of the A1 mode in terms of the propagation time and frequency, wherein the A1 mode is converted to a fundamental symmetric (S0) mode in a peeling section and converted back to the A1 mode after the peeling section, wherein the propagation time changes due to the mode conversion in the peeling section as compared to the propagation time in the absence of the peeling section, and wherein the propagation time of the A1 mode decreases as the length of the peeling section increases, (4) generating reference data indicating relationships between the propagation time and the frequency of the A1 mode for different lengths of the peeling section based on the process (3), and (5) determining the length of an unknown peeling section by comparing measured data to the reference data.

2. The system for damage diagnosis according to claim 1, wherein the references data is configured to illustrate a rate of change in the frequency with respect to the propagation time for the A1 mode for each of different lengths of the peeling section.

3. The system for damage diagnosis according to claim 1, wherein the A1 mode includes a plurality of waves having mutually different frequencies; and the propagation time of the A1 mode is a propagation time of a maximum intensity portion of at least one of the plurality of waves.

4. The system for damage diagnosis according to claim 1, wherein the processing unit, in the oscillation control process, controls the two oscillators so that an symmetric mode is canceled out and an asymmetric mode is emphasized by adding the broadband Lamb waves.

5. The system for damage diagnosis according to claim 1, wherein
the time-frequency transformation is any one of the wavelet transformation, short-time Fourier transformation, chirplet transformation, Wigner transformation, and Stockwell transformation, or a combination of any two or more of said transformations.

6. The system for damage diagnosis according to claim 1, wherein
the oscillator is attached to the object.

7. The system for damage diagnosis according to claim 1, wherein
the oscillation detection sensor is attached to the object.

8. A method for damage diagnosis for diagnosing damage on or within an object constructed of a Carbon Fiber Reinforced Plastic (CFRP) material, the method using:
- two oscillators, each oscillator comprising an MFC (Macro Fiber Composite) actuator having a piezoelectric element, with one oscillator being attached to one surface, and the other oscillator being attached to a second, opposing surface in the thickness direction of the object, for applying a broadband ultrasonic oscillation to the object to generate in the object a broadband Lamb wave comprising at least a one-dimensional asymmetric (A1) mode by causing strain orthogonal to an axial direction of the piezoelectric element, which is a direction parallel to a direction of wave propagation;
- an oscillation detection sensor comprising an FBG (Fiber Bragg Grating) optical fiber placed near a location of the damage diagnoses, for detecting the broadband Lamb wave propagating through the object by detecting strain occurring in an axial direction of the FBG optical fiber;
- a spectrum analyzer, connected to the oscillation detection sensor, comprising a light source that includes all oscillation areas of reflected wavelengths of the oscillation detection sensor; and
- a processing unit, being connected to the oscillator, the spectrum analyzer, and the oscillation detection sensor, the method comprising:
(1) executing an oscillation control process to control the oscillators, wherein the processing unit controls the two oscillators so that an asymmetrical mode Lamb wave having directivity, is generated in the object,
(2) obtaining, via output wave data acquired from the spectrum analyzer, a two-dimensional propagation intensity distribution of the broadband Lamb wave according to propagation time and frequency based on a time-frequency transformation,
(3) analyzing a portion of the two-dimensional propagation intensity distribution, the portion indicating the propagation of the A1 mode in terms of the propagation time and frequency, wherein the A1 mode is converted to a fundamental symmetric (S0) mode in a peeling section and converted back to the A1 mode after the peeling section, wherein the propagation time changes due to the mode conversion in the peeling section as compared to the propagation time in the absence of the peeling section, and wherein the propagation time of the A1 mode decreases as the length of the peeling section increases,
(4) generating reference data indicating relationships between the propagation time and the frequency of the A1 mode for different lengths of the peeling section based on the process (3), and
(5) determining the length of an unknown peeling section by comparing measured data to the reference data.

9. The method for damage diagnosis according to claim 8, wherein
the references data is configured to illustrate a rate of change in the frequency with respect to the propagation time for the A1 mode for each of different lengths of the peeling section.

10. The method for damage diagnosis according to claim 8, wherein
the time-frequency transformation is any one of the wavelet transformation, short-time Fourier transformation, chirplet transformation, Wigner transformation, and Stockwell transformation, or a combination of any two or more of said transformations.

* * * * *